US011963856B2

(12) United States Patent
Lee et al.

(10) Patent No.: US 11,963,856 B2
(45) Date of Patent: Apr. 23, 2024

(54) ABSORBENT ARTICLE

(71) Applicant: Kimberly-Clark Worldwide, Inc., Neenah, WI (US)

(72) Inventors: JuHyung Lee, Suwon-si (KR); KueYoung You, Seongnam-si (KR); SungSu Kim, Yongin-si (KR); SeoYeon Son, Seongnam-si (KR); HakJae Kim, Yongin-si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 532 days.

(21) Appl. No.: 17/295,331

(22) PCT Filed: Nov. 28, 2018

(86) PCT No.: PCT/US2018/062802
§ 371 (c)(1),
(2) Date: May 19, 2021

(87) PCT Pub. No.: WO2020/112102
PCT Pub. Date: Jun. 4, 2020

(65) Prior Publication Data
US 2022/0015962 A1  Jan. 20, 2022

(51) Int. Cl.
*A61F 13/511* (2006.01)
*A61F 13/472* (2006.01)
(Continued)

(52) U.S. Cl.
CPC ...... *A61F 13/51104* (2013.01); *A61F 13/472* (2013.01); *A61F 13/4757* (2013.01);
(Continued)

(58) Field of Classification Search
CPC .............. A61F 13/4704; A61F 13/4751; A61F 13/4755; A61F 13/4756; A61F 13/4757;
(Continued)

(56) References Cited

U.S. PATENT DOCUMENTS

| H1377 H | 11/1994 | Perry |
|---|---|---|
| 5,891,118 A | 4/1999 | Toyoshima et al. |

(Continued)

FOREIGN PATENT DOCUMENTS

| CN | 105228570 A | 1/2016 |
|---|---|---|
| CN | 108601683 A | 9/2018 |

(Continued)

OTHER PUBLICATIONS

GDM, "Lady sanitary napkins airlaid", 2017, GDM, a Coesia Company, http://www.gdm-spa.com/en/home/products/product_lady/product_lady-sanitary-napkins-airlaid.

*Primary Examiner* — Catharine L Anderson
*Assistant Examiner* — Lynne Anderson
(74) *Attorney, Agent, or Firm* — KIMBERLY-CLARK WORLDWIDE, INC.

(57) ABSTRACT

An absorbent article which can have an improved feeling of comfort next to the skin of the wearer and a reduction in the feelings of wetness and rewet. An absorbent article can have a longitudinal direction, a transverse direction, and a depth direction. The absorbent article can have a topsheet layer, a backsheet layer, and an absorbent core positioned between the topsheet layer and the backsheet layer. The topsheet layer can have a hydrophilic central layer, a semi-hydrophilic first side layer, and a semi-hydrophilic second side layer. Each of the semi-hydrophilic side layers can be bonded to the central layer utilizing an embossing technique in the regions of overlap of each of the semi-hydrophilic side layers with the central layer. The area of the body-facing surface of each of the regions of overlap can contain from about 10% to about 35% of at least one embossment.

14 Claims, 20 Drawing Sheets

(51) Int. Cl.
*A61F 13/475* (2006.01)
*A61F 13/513* (2006.01)
*A61F 13/15* (2006.01)
*A61F 13/51* (2006.01)
*A61F 13/537* (2006.01)

(52) U.S. Cl.
CPC .... *A61F 13/5116* (2013.01); *A61F 13/51305* (2013.01); *A61F 2013/15512* (2013.01); *A61F 2013/51033* (2013.01); *A61F 2013/51066* (2013.01); *A61F 2013/51338* (2013.01); *A61F 2013/53795* (2013.01)

(58) Field of Classification Search
CPC .......... A61F 13/49406; A61F 13/49446; A61F 13/5116; A61F 13/51305; A61F 2013/51078; A61F 2013/51808; A61F 2013/51083; A61F 2013/51088
See application file for complete search history.

(56) References Cited

U.S. PATENT DOCUMENTS

| | | | |
|---|---|---|---|
| 5,961,505 A | 10/1999 | Coe et al. | |
| 6,017,336 A | 1/2000 | Sauer | |
| 7,166,094 B2 | 1/2007 | Glaug et al. | |
| 7,291,763 B2 | 11/2007 | Mirle et al. | |
| 7,388,123 B2 | 6/2008 | Cowell et al. | |
| 7,429,689 B2 | 9/2008 | Chen et al. | |
| 7,432,412 B2 | 10/2008 | Kigata et al. | |
| 7,625,363 B2 | 12/2009 | Yoshimasa et al. | |
| 8,466,334 B2 | 6/2013 | Takeuchi et al. | |
| 9,173,786 B2 | 11/2015 | Roh et al. | |
| 9,220,646 B2 | 12/2015 | Lee et al. | |
| 9,283,127 B2 | 3/2016 | Lee | |
| 9,456,932 B2 | 10/2016 | Digiacomantonio et al. | |
| 9,949,880 B2 * | 4/2018 | Wang | A61F 13/4751 |
| 9,987,176 B2 | 6/2018 | Roe et al. | |
| 11,324,644 B2 * | 5/2022 | Kurihara | A61F 13/51108 |
| 2004/0087924 A1 | 5/2004 | Sroda et al. | |
| 2004/0267220 A1 | 12/2004 | Hull et al. | |
| 2006/0100598 A1 | 5/2006 | Tamura et al. | |
| 2006/0135931 A1 | 6/2006 | Suzuki et al. | |
| 2010/0168707 A1 * | 7/2010 | Nishikawa | A61F 13/4704 604/385.04 |
| 2011/0046592 A1 | 2/2011 | Nishikawa et al. | |
| 2011/0319855 A1 | 12/2011 | Lash | |
| 2012/0265161 A1 | 10/2012 | Banks et al. | |
| 2015/0313769 A1 | 11/2015 | Dahl et al. | |
| 2017/0354549 A1 | 12/2017 | Cho et al. | |
| 2021/0045940 A1 * | 2/2021 | Nagashima | A61F 5/4401 |
| 2021/0282982 A1 * | 9/2021 | Yoshiba | A61F 13/513 |

FOREIGN PATENT DOCUMENTS

| | | |
|---|---|---|
| CN | 108882998 A | 11/2018 |
| EP | 0963745 B1 | 2/2003 |
| GB | 428344 A | 5/1935 |
| JP | 2007330822 A | 12/2007 |
| RU | 2176492 C2 | 12/2001 |
| RU | 2625434 C2 | 7/2017 |

\* cited by examiner

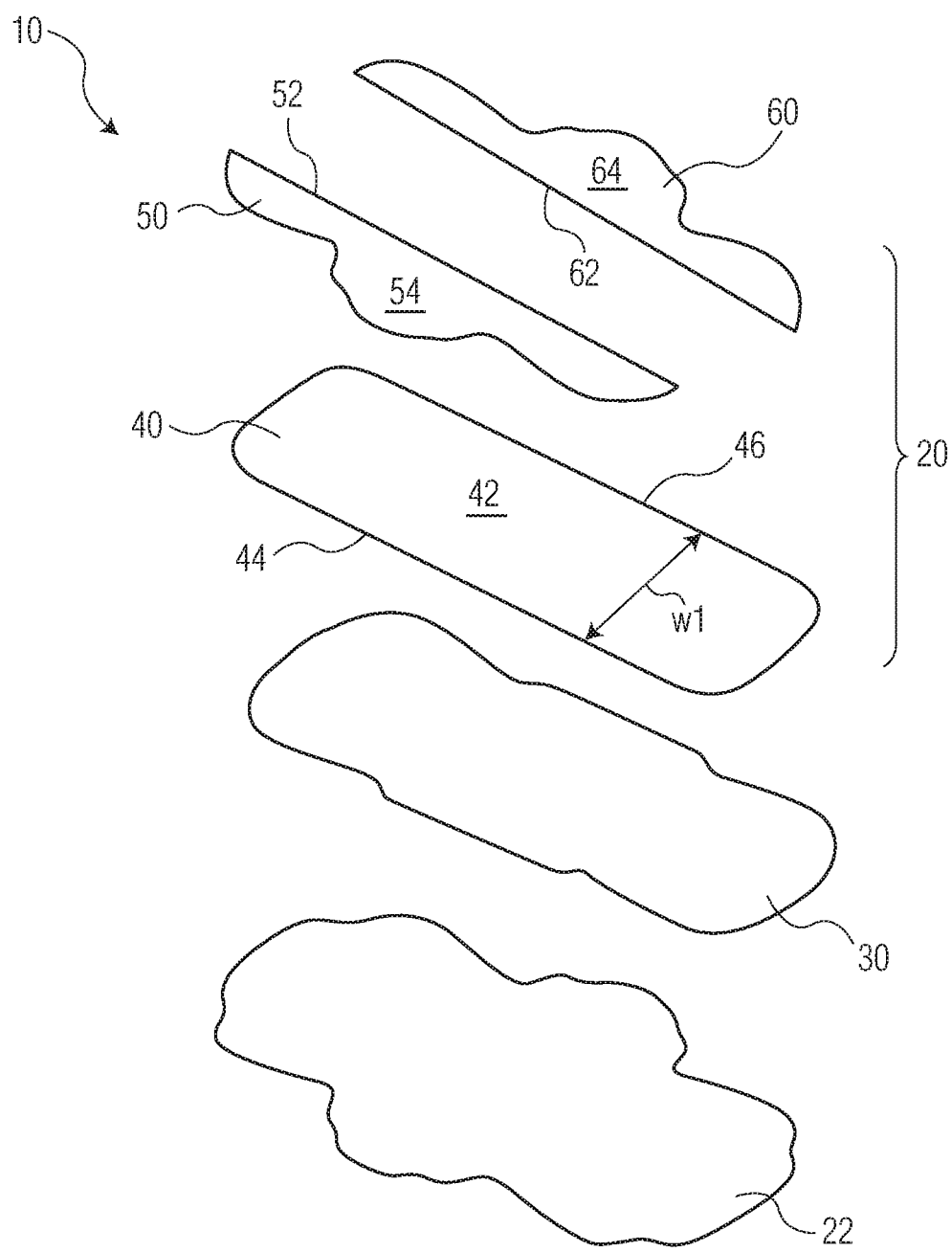
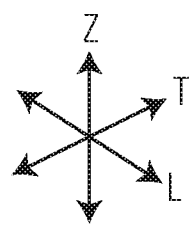
FIG. 2

ABSORBENT ARTICLE

BACKGROUND OF THE DISCLOSURE

Products such as absorbent articles are often used to collect and retain human body exudates containing, for example, urine, menses and/or blood. Comfort, absorbency, and discretion are three main product attributes and areas of concern for the wearer of the product. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, pantiliners, and incontinence devices. These products generally have an absorbent core positioned between a body-facing liquid permeable topsheet layer and a garment-facing liquid impermeable backsheet layer. The edges of the topsheet and the backsheet layers are often bonded together at their periphery to form a seal to contain the absorbent core and body exudates received into the product through the topsheet layer. In use, such products are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

Wearers of such conventional absorbent products are interested in having such products demonstrate reduced feelings of wetness once the product has been soiled or insulted during use. Unfortunately, once such a product has been soiled, the topsheet layer often remains wet or at least feels wet for some time throughout the period of use. The topsheet layer may frequently be absorbent, being made from hydrophilic construction materials, such as natural fibers or surfactant-treated polymeric materials. These materials often retain at their surface some noticeable moisture following soiling, thereby creating the uncomfortable wetness sensation during continued use of the product. While in an ideal situation, such products are replaced by the user once soiling actually occurs, in some instances, the user may not initially recognize that soiling has occurred. Upon such realization, the user may not be in a location where a change of product is possible or convenient. The frequent replacement of these products may also be impractical given a user's particular daily activities even if wetness is detected immediately following soiling.

As a result of the desire of wearers to experience a reduced wetness sensation from a product during prolonged use (for both skin-health rationale as well as physical comfort), manufacturers have explored numerous technological approaches to address these feelings following soiling of the product. Manufacturers have attempted to reduce both the initial feelings of wetness and also continuing sensations of "rewet" wherein the product absorbs fluid or liquid such as menses or urine through the topsheet layer and delivers it to an interior layer of the absorbent article and subsequently releases the fluid or liquid under the continuing pressure of wear back to the topsheet layer from the interior layer. This release of fluid/liquid back to the topsheet layer often leads to the wearer's perception of continuing wetness. Manufacturers of such products have specifically designed individual topsheet layers for reduced wetness (and rewet) based on chemical enhancements to the topsheet layer. In this regard, hydrophobic topsheet layers have been developed from polymer fibrous nonwoven layers or aperture film layers such that the product demonstrates an extended feeling of dryness at the skin-contacting surface of the product. Further, liquid/fluid that is retained in the interior layers of the product may have less of a propensity to pass back through the topsheet layer to the weaerer's skin as a result of the hydrophobic interior surface properties of the topsheet layer. In some instances, therefore, the topsheet layer acts as a one-way valve allowing moisture to pass in one direction and keeping it below the user-facing, skin-contacting surface. However, such hydrophobic, film-based materials utilized for the topsheet layer have often provided an uncomfortable, "plastic"-like feel to the product.

As a result, there remains a need for an improved product, such as an absorbent article, which has an improved feeling of comfort next to the skin of the wearer and has a reduction in the feelings of wetness and rewet.

SUMMARY OF THE DISCLOSURE

In various embodiments, an absorbent article characterized by can have a longitudinal direction, a transverse direction, and a depth direction; a longitudinal centerline and a transverse centerline; a first transverse direction end edge and a second transverse direction end edge; an opposing pair of longitudinal direction side edges extending between and connecting the first transverse direction end edge and the second transverse direction end edge; an anterior region, a posterior region, and a central region between the anterior region and the posterior region; a topsheet layer which can have a hydrophilic central layer extending in the longitudinal direction of the absorbent article and symmetrically straddling the longitudinal centerline, the central layer having a first longitudinal direction side edge and a second longitudinal direction side edge; a semi-hydrophilic first side layer having a first inner edge and in an overlapping configuration with the central layer such that the first inner edge of the first side layer is positioned closer in the transverse direction to the longitudinal centerline than the first longitudinal direction side edge of the central layer; and a semi-hydrophilic second side layer having a second inner edge and in an overlapping configuration with the central layer such that the second inner edge of the second side layer is positioned closer in the transverse direction to the longitudinal centerline than the second longitudinal direction side edge of the central layer; a first region of overlap bordered by the first longitudinal direction side edge of the central layer, the first inner edge of the first side layer, a first portion of the first transverse direction end edge of the absorbent article, and a first portion of the second transverse direction end edge of the absorbent article; a second region of overlap bordered by the second longitudinal direction side edge of the central layer, the second inner edge of the second side layer, a second portion of the first transverse direction end edge of the absorbent article, and a second portion of the second transverse direction end edge of the absorbent article; a first body facing surface of the first region of overlap has a first area wherein from 10% to 35% of the first area contains a first embossment; a second body facing surface of the second region of overlap has a second area wherein 10% to 35% of the second area contains a second embossment; a backsheet layer; and an absorbent core positioned between the topsheet layer and the backsheet layer and having a first depression located in the depth direction beneath the first embossment and a second depression located in the depth direction beneath the second embossment.

In various embodiments, the hydrophilic central layer has a water contact angle at or below 59°. In various embodiments, each of the semi-hydrophilic first side layer and semi-hydrophilic second side layer have a water contact angle from 60° to 89°.

In various embodiments, the topsheet layer comprises an exposed region which has a width in the transverse direction between the first inner edge of the first side layer and the second inner edge of the second side layer of from 10 mm to 40 mm. In various embodiments, the first region of overlap has a width in the transverse direction between the first longitudinal direction side edge of the central layer and the first inner edge of the first side layer of greater than 10 mm. In various embodiments, the second region of overlap has a width in the transverse direction between the second longitudinal direction side edge of the central layer and the second inner edge of the second side layer of greater than 10 mm.

In various embodiments, the first embossment extends in the longitudinal direction of the absorbent article and has a portion located in each of the anterior region, posterior region, and central region of the first region of overlap and wherein the second embossment extends in the longitudinal direction of the absorbent article and has a portion located in each of the anterior region, posterior region, and central region of the second region of overlap. In various embodiments, the absorbent article can further have a first plurality of discrete embossments located in the central region of the first region of overlap and a second plurality of discrete embossment located in the central region of the second region of overlap. In various embodiments, the absorbent article can further have a first plurality of discrete embossments evenly distributed throughout the anterior region, posterior region, and central region of the first region of overlap and a second plurality of discrete embossments evenly distributed through the anterior region, posterior region, and central region of the second region of overlap.

In various embodiments, the first embossment crosses over the first inner edge of the first side layer and connects to a first secondary embossment positioned in the anterior region of the exposed region, the first embossment crossed over the first inner edge of the first side layer and connects to a second secondary embossment positioned in the posterior region of the exposed region, wherein the second embossment crosses over the second inner edge of the second side layer and connects to the first secondary embossment in the anterior region, and wherein the second embossment crosses over the second inner edge of the second side layer and connected to the second secondary embossment in the posterior region.

In various embodiments, the absorbent article can have a secondary embossment in the exposed region. In various embodiments, the absorbent article can further have a surge layer. In various embodiments, the absorbent article can further have a fluid intake layer. In various embodiments, the absorbent article can further have a distribution layer.

BRIEF DESCRIPTION OF DRAWINGS

FIG. 2 is an exploded perspective view of the absorbent article of FIG. 1.

Figure 1:
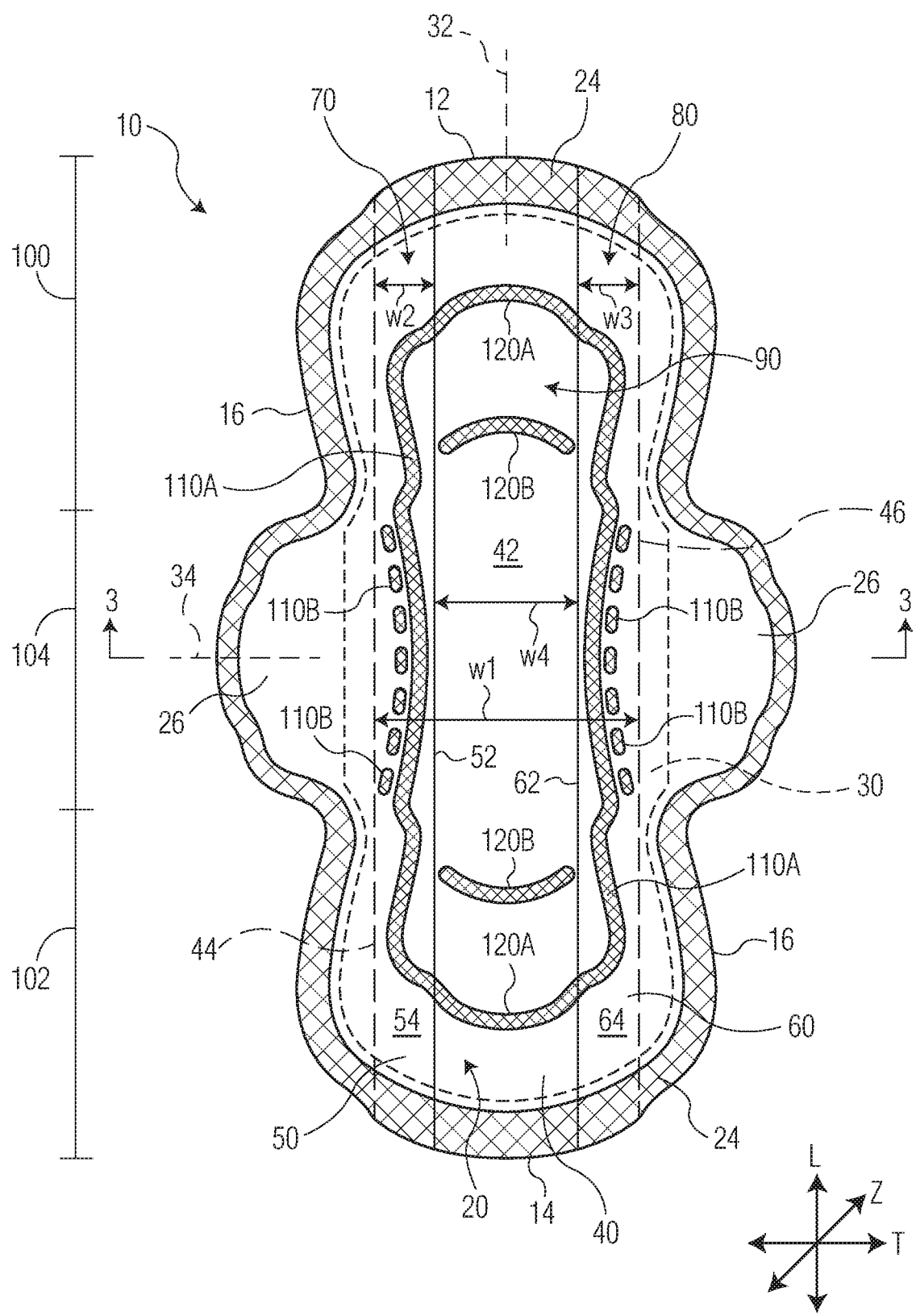
FIG. 1 is a top down view of an embodiment of an absorbent article.

Repeat use of reference characters in the present specification and drawings is intended to represent the same or analogous features or elements of the disclosure.

DETAILED DESCRIPTION OF THE DISCLOSURE

The present disclosure is generally directed towards an absorbent article which can have an improved feeling of comfort next to the skin of the wearer and a reduction in the feelings of wetness and rewet. An absorbent article can have a longitudinal direction, a transverse direction, and a depth direction. The absorbent article can have a topsheet layer, a backsheet layer, and an absorbent core positioned between the topsheet layer and the backsheet layer. The topsheet layer can have a hydrophilic central layer, a semi-hydrophilic first side layer, and a semi-hydrophilic second side layer. Each of the semi-hydrophilic side layers can be bonded to the central layer utilizing an embossing technique in the regions of overlap of each of the semi-hydrophilic side layers with the central layer. The area of the body-facing surface of each of the regions of overlap can contain from about 10% to about 35% of at least one embossment.

Definitions

As used herein, the term "absorbent article" refers herein to a garment or other end-use personal care absorbent article, including, but not limited to, catamenial products, such as sanitary napkins, feminine pads, pantiliners, and panty shields, incontinence devices, and the like.

As used herein, the term "airlaid" refers herein to a web manufactured by an airlaying process. In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers herein to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form one fiber. Conjugate fibers are also sometimes referred to as bicomponent fibers or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea" arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al. each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "hydrophilic" refers to surfaces with a water contact angle at or below 59°.

As used herein, the term "hydrophobic" refers to surfaces with the property to repel fluid with a water contact angle at or greater than 90°.

As used herein, the term "semi-hydrophilic" refers to surfaces with a water contact angle from 60° to 89°.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10 or 20 gsm to about 120, 125 or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent" or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in part on ionicity (a factor of the ionic concentration of the aqueous solution), and the SAP functional polar groups that have an affinity for water. SAP are typically made from the polymerization of acrylic acid blended with sodium hydroxide in the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating on another material or fiber.

Absorbent Article:

The present disclosure is generally directed towards an absorbent article which can have an improved feeling of comfort next to the skin of the wearer and a reduction in the feelings of wetness and rewet. An absorbent article can have a longitudinal direction, a transverse direction, and a depth direction. The absorbent article can have a topsheet layer, a backsheet layer, and an absorbent core positioned between the topsheet layer and the backsheet layer. The topsheet layer can have a hydrophilic central layer, a semi-hydrophilic first side layer, and a semi-hydrophilic second side layer. Each of the semi-hydrophilic side layers can be bonded to the central layer utilizing an embossing technique in the regions of overlap of each of the semi-hydrophilic side layers with the central layer. The area of the body-facing surface of each of the regions of overlap can contain from about 10% to about 35% of at least one embossment.

Figure 3:
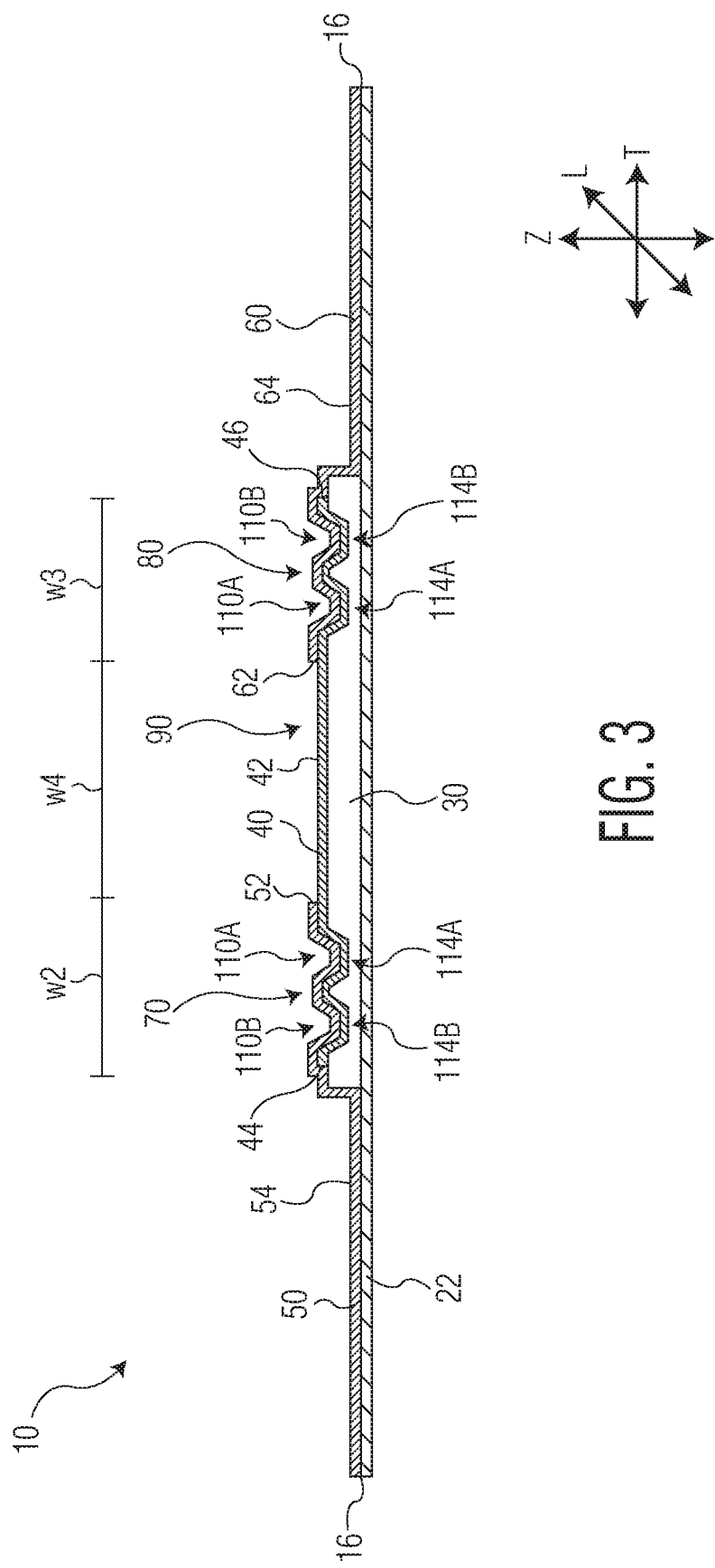
FIG. 3 is a cross-sectional view of the absorbent article of FIG. 1 taken along line 3-3.

Referring to FIGS. 1-3, FIG. 1 provides an illustration of a top down view of an exemplary absorbent article 10, FIG. 2 provides an illustration of an exploded perspective view of the absorbent article 10 of FIG. 1, and FIG. 3 provides an illustration of a cross-sectional view of the absorbent article 10 of FIG. 1 taken along line 3-3. The absorbent article 10 can have a longitudinal direction (L), a transverse direction (T), and a depth direction (Z). The absorbent article 10 can have a first transverse direction end edge 12, a second transverse direction end edge 14 opposite the first transverse direction end edge 12, and a pair of opposing longitudinal direction side edges 16 extending between and connecting the first transverse direction end edge 12 and the second transverse direction end edge 14. In various embodiments, the absorbent article 10 can take on various geometries but will generally have a pair of opposing longitudinal direction side edges 16 and a pair of opposing transverse direction end edges 12 and 14. The absorbent article 10 can have a wearer facing, liquid permeable topsheet layer 20 and a garment facing, liquid impermeable backsheet layer 22. An absorbent core 30 can be positioned between the topsheet layer 20 and the backsheet layer 22. The absorbent article 10 can have a longitudinal centerline 32 and a transverse centerline 34.

The topsheet layer 20 and the backsheet layer 22 can both extend beyond the outermost peripheral edges of the absorbent core 30 and can be peripherally bonded together, either entirely or partially, using known bonding techniques to form a sealed peripheral region 24. For example, the topsheet layer 20 and the backsheet layer 22 can be bonded together by adhesive bonding, ultrasonic bonding, or any other suitable bonding method known in the art.

In various embodiments, the absorbent article 10 can have a pair of wings 26 extending outwardly, in the transverse direction T, from the absorbent article 10. The wings 26 can drape over the edges of the wearer's undergarment so that the wings 26 are disposed between the edges of the wearer's undergarment and her thighs. The wings 26 can serve at least two purposes. First, the wings 26 can prevent soiling of the wearer's undergarment by forming a barrier along the edges of the undergarment. Second, the wings 26 can be provided with an attachment aid (not shown), such as, for example, a garment attachment adhesive or a hook, to keep the absorbent article 10 securely and properly positioned in the undergarment. The wings 26 can wrap around the crotch region of the wearer's undergarment to aid in securing the absorbent article 10 to the wearer's undergarment when in use. Each wing 26 can fold under the crotch region of the wearer's undergarment and the attachment aid can either form a secure attachment to the opposite wing 26 or directly to the surface of the wearer's undergarment. In various embodiments, the wings 26 can be an extension of materials forming the topsheet layer 20 and/or the backsheet layer 22, such that the wings 26 can be of a unitary construction with the absorbent article 10. In various embodiments, the wings 26 can be constructed of materials similar to the topsheet layer 20, the backsheet layer 22 or combinations of these materials. In various embodiments, the wings 26 can be separate elements bonded to the main body of the absorbent article 10. It is to be understood that the wings 26 are optional and, in various embodiments, an absorbent article 10 can be configured without wings 26.

Each of these components of the absorbent article 10, as well as additional components, will be described in more detail herein.

Topsheet Layer:

The topsheet layer 20 defines a wearer facing surface of the absorbent article 10 that may directly contact the body of the wearer and is liquid permeable to receive body exudates. The topsheet layer 20 is desirably provided for comfort and conformability and functions to direct body exudates away from the body of the wearer, through its own structure, and towards the absorbent core 30. The topsheet layer 20 desirably retains little to no liquid in its structure, so that it provides a relatively comfortable and non-irritating surface next to the skin of the wearer of the absorbent article 10. The topsheet layer 20 includes a central layer 40 positioned in an overlapping configuration with first and second opposing side layers, 50 and 60.

Referring to FIGS. 1-3, the central layer 40 can extend in the longitudinal direction (L) of the absorbent article 10 and can be positioned along and symmetrically straddling the longitudinal centerline 32 of the absorbent article 10. The central layer 40 can have a first longitudinal direction side edge 44 and a second longitudinal direction side edge 46 and a width W1 in the transverse direction (T) extending between the first longitudinal direction side edge 44 and the second longitudinal direction side edge 46. In various embodiments, the width W1 between the first longitudinal direction side edge 44 of the central layer 40 and the second longitudinal direction side edge 46 of the central layer 40 can be greater than about 50 mm. In various embodiments, the width W1 between the first longitudinal direction side edge 44 of the central layer 40 and the second longitudinal direction side edge 46 of the central layer 40 can be from about 50 or 60 mm to about 70 or 80 mm.

A first side layer 50 can be positioned in an overlapping configuration with the central layer 40 such than an inner edge 52 of the first side layer 50 can be positioned between the first longitudinal direction side edge 44 of the central layer 40 and the longitudinal centerline 32 of the absorbent article 10. Thus, the inner edge 52 of the first side layer 50 is positioned transversely closer to the longitudinal centerline 32 of the absorbent article 10 than the first longitudinal direction side edge 44 of the central layer 40. A second side layer 60 can be positioned in an overlapping configuration with the central layer 40 such that an inner edge 62 of the second side layer 60 can be positioned between the second longitudinal direction side edge 46 of the central layer 40 and the longitudinal centerline 32 of the absorbent article 10. Thus, the inner edge 62 of the second side layer 60 is positioned transversely closer to the longitudinal centerline 32 of the absorbent article 10 than the second longitudinal direction side edge 46 of the central layer 40. The topsheet layer 20 can, therefore, have a central layer 40 which is overlapped by each of the first side layer 50 and the second side layer 60.

The overlapping configuration of the first side layer 50 over the central layer 40 can result in a first region of overlap 70. The first region of overlap 70 exists where the material forming the central layer 40 is overlapped by the material forming the first side layer 50. In various embodiments in which the first side layer 50 and the central layer 40 have a length extending in the longitudinal direction (L) from the first transverse direction end edge 12 to the second transverse direction end edge 14, the first region of overlap 70 can be bounded by the first longitudinal direction side edge 44 of the central layer 40, the inner edge 52 of the first side layer 50, a portion of the first transverse direction end edge 12 of the absorbent article 10, and a portion of the second transverse direction end edge 14 of the absorbent article 10. The first region of overlap 70 can have a width W2 in the transverse direction (T) extending between the first longitudinal direction side edge 44 of the central layer 40 and the inner edge 52 of the first side layer 50. In various embodiments, the width W2 of the first region of overlap 70 can be uniform in the longitudinal direction (L) of the absorbent article 10. In various embodiments, the width W2 of the first region of overlap 70 can be variable in the longitudinal direction (L) of the absorbent article 10. In various embodiments, the width W2 of the first region of overlap 70 is greater than about 10 mm. In various embodiments, the width W2 of the first region of overlap 70 is from about 10, 12, or 14 mm to about 16, 18, or 20 mm.

The overlapping configuration of the second side layer 60 over the central layer 40 can result in a second region of overlap 80. The second region of overlap 80 exists where the material forming the central layer 40 is overlapped by the material forming the second side layer 60. In various embodiments in which the second side layer 60 and the central layer 40 have a length extending in the longitudinal direction (L) from the first transverse direction end edge 12 to the second transverse direction end edge 14, the second region of overlap 80 can be bounded by the second longitudinal direction side edge 46 of the central layer 40, the inner edge 62 of the second side layer 60, a portion of the first transverse direction end edge 12 of the absorbent article 10, and a portion of the second transverse direction end edge 14 of the absorbent article 10. The second region of overlap 80 can have a width W3 in the transverse direction (T) extending between the second longitudinal direction side edge 46 of the central layer 40 and the inner edge 62 of the second side layer 60. In various embodiments, the width W3 of the second region of overlap 80 can be uniform in the longitudinal direction (L) of the absorbent article 10. In various embodiments, the width W3 of the second region of overlap 80 can be variable in the longitudinal direction (L) of the absorbent article 10. In various embodiments, the width W3 of the second region of overlap 80 is greater than about 10 mm. In various embodiments, the width W3 of the second region of overlap 80 is from about 10, 12, or 14 mm to about 16, 18, or 20 mm.

As the topsheet layer 20 can have a first region of overlap 70 and a second region of overlap 80, the topsheet layer 20 can also have a region, an exposed region 90, wherein the central layer 40 is not overlapped by either the first side layer 50 or the second side layer 60. Rather, the exposed region 90 of the central layer 40 can have a body facing surface 42 which can be exposed to the body of the wearer of the absorbent article 10 and can come into direct contact with the body of the wearer of the absorbent article 10. In various embodiments wherein the central layer 40, the first side layer 50, and the second side layer 60 each have a length in the longitudinal direction (L) of the absorbent article 10 extending from the first transverse direction end edge 12 to the second transverse direction end edge 14, the exposed region 90 of the central layer 40 can be bordered by the inner edge 52 of the first side layer 50, the inner edge 62 of the second side layer 60, a portion of the first transverse direction end edge 12 of the absorbent article 10, and a portion of the second transverse direction end edge 14 of the absorbent article 10. The exposed region 90 can have a width W4 in the transverse direction (T) extending between the inner edge 52 of the first side layer 50 and the inner edge 62 of the second side layer 60. In various embodiments, the width W4 of the exposed region 90 can be less than about 40 mm. In various embodiments, the width W4 of the exposed region 90 can be from about 10 or 20 mm to about 30 or 40 mm. In various embodiments, the width W4 of the exposed region 90 can be from about 30 mm to about 40 mm.

The central layer 40 of the topsheet layer 20 can be constructed of any woven, nonwoven, or film sheet material which is easily penetrated by bodily exudates which may contact the body-facing surface 42 of the central layer 40. In various embodiments, the central layer 40 can be constructed from various nonwoven webs such as meltblown webs, spunbond webs, hydroentangled spunlace webs, or through air bonded carded webs. Examples of suitable central layer 40 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a material suitable for use as a central layer 40 is a perforated polyethylene film material. An example of a suitable central layer 40 can be a bonded carded web made of polypropylene and polyethylene such as that obtainable from Sandler Corporation, Germany. U.S. Pat. No. 4,801,494 to Datta, et al., and U.S. Pat. No. 4,908,026 to Sukiennik, et al., and WO 2009/062998 to Texol teach various other materials that may be used as the central layer 40, each of which is hereby incorporated by reference thereto in its entirety. Additional central layer 40 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

In various embodiments, the central layer 40 may contain a plurality of apertures (not shown) formed therethrough to permit body exudates to pass more readily into the absorbent core 30. The apertures may be randomly or uniformly arranged throughout the central layer 40 of the topsheet layer 20 or they may be located in a narrow longitudinal band or strip arranged along the longitudinal centerline 32 of the absorbent article 10. The size, shape, diameter, and number of apertures may be varied to suit an absorbent article's 10 particular needs.

In various embodiments, the central layer 40 can have a basis weight ranging from about 5, 10, 15, 20 or 25 gsm to about 50, 100, 120, 125 or 150 gsm. For example, in an embodiment, a central layer 40 can be constructed from a through air bonded carded web having a basis weight ranging from about 15 gsm to about 100 gsm. In another example, a central layer 40 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics and others. Alternatively, apertured films, such as those available from such film suppliers as Texol, Italy and Tredegar, U.S.A. may be utilized. In various embodiments, the central layer 40 can be constructed from a perforated polyethylene film having a basis weight from about 15 gsm to about 30 gsm. In various embodiments, the central layer 40 can be constructed from a cotton material and have a basis weight from about 25 gsm to about 35 gsm.

In various embodiments, the central layer 40 of the topsheet layer 20 is hydrophilic and has a water contact angle of less than 59°. The central layer 40 can be formed from a material which is inherently hydrophilic or can be formed from a hydrophobic material which has then been treated with a hydrophilic coating such as, for example, a surfactant treatment.

Each of the first side layer 50 and the second side layer 60 can be constructed of any woven, nonwoven, or film sheet materials that can be the same as or different from the material selected to form the central layer 40 of the topsheet layer 20. The selection of the particular materials for forming the first side layer 50 and the second side layer 60 can vary based upon the overall desired attributes of the first side layer 50 and the second side layer 60. For example, it may be desired to have a hydrophilic material forming the central layer 40 and semi-hydrophilic barrier type materials forming each of the first side layer 50 and the second side layer 60 to prevent leakage and increase a sense of dryness in the area of each of the first side layer 50 and the second side layer 60. For example, various nonwoven fabrics or webs such as meltblown webs, spunbond webs, or through-air bonded carded webs (TABCW) can be utilized to form each of the first side layer 50 and the second side layer 60. In various embodiments, each of the first side layer 50 and the second side layer 60 have semi-hydrophilic barrier properties in which the materials forming the first side layer 50 and the second side layer each have a water contact angle from 60° or 70° to 80° or 89°.

Each of the first side layer 50 and the second side layer 60 can be bonded to the central layer 40 utilizing an embossing technique. In various embodiments, in additional to utilizing an embossing technique, each of the first side layer 50 and the second side layer 60 can also be adhesively, thermally, or ultrasonically, bonded to the central layer 40. Traditional absorbent article construction adhesive may be used to bond the first side layer 50 and the second side layer 60 the central layer 40. Either of the central layer 40 and/or the first or second side layers, 50 and/or 60, may be treated with surfactants and/or skin-health benefit agents, as are well known in the art.

Such longitudinally directed first side layer 50 and second side layer 60 can be of a single or multi-layered construction. In various embodiments, the first side layer 50 and the second side layer 60 are formed from a single layer construction. In various embodiments, the first side layer 50 and the second side layer 60 are formed from combining a mixture of hydrophilic and hydrophobic fibers together. For example, in various embodiments, the first side layer 50 and the second side layer 60 can be formed by combining 30% hydrophobic fibers and 70% hydrophilic fibers together and forming a TABCW material. In various embodiments, the first side layer 50 and the second side layer 60 can be formed by combining 50% hydrophobic fibers and 50% hydrophilic fibers together and forming a TABCW material. In various embodiments, the first side layer 50 and the second side layer 60 can be adhesively or otherwise bonded laminates. In various embodiments, the first side layer 50 and the second side layer 60 can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as a polyethylene having a basis weight from about 10 to about 40 gsm. Construction adhesive can be utilized to laminate the spunbond layer to the film layer at an add-on level of between about 0.1 gsm and 15 gsm. The film layer may also serve as a barrier layer to prevent rewet of the first side layer 50 and the second side layer 60 as well as to prevent the flow of fluid off the side edges of the absorbent article 10. In various embodiments, the first side layer 50 and the second side layer 60 can be laminates such as a spunbond-meltblown-meltblown-spunbond layer ("SMMS") laminate, spunbond-film laminate, or alternatively, other nonwoven laminate combinations.

As described herein, the central layer 40 can have hydrophilic properties wherein the material forming the central layer 40 has a water contact angle less than 59° and each of the first side layer 50 and the second side layer 60 can have semi-hydrophilic properties wherein the material forming each of the first side layer 50 and the second side layer 60 can have a water contact angle from 60° or 70° to 80° or 89°. A central layer 40 having hydrophilic properties can facilitate the intake of bodily exudates from the body facing surface 42 of the central layer 40 and into an interior layer of the absorbent article 10 such as the absorbent core 30. A hydrophilic central layer 40 formed from a soft or gentle-to-the-skin material such as a TABCW or cotton material, however, can provide the wearer of the absorbent article 10 with a feeling of wetness as the bodily exudates may remain associated with the hydrophilic central layer 40 or the bodily exudates may migrate from an interior layer of the absorbent article 10 back to the hydrophilic central layer 40. A hydrophilic central layer 40 formed from a film material can provide the wearer with a feeling of dryness, however, the film material may cause skin irritation to the wearer of the absorbent article 10. To provide an absorbent article 10 that can intake bodily exudates with a reduction in the feeling of wetness and/or a reduction in skin irritation, each of the first side layer 50 and the second side layer 60 overlap the hydrophilic central layer 40 such that a width W4 in the transverse direction (T) of exposed region 90 of the central layer 40 is less than 40 mm.

A first side layer 50 and a second side layer 60 having semi-hydrophilic properties can also facilitate the intake of any bodily exudates which come into contact with either or both of the first side layer 50 and/or the second side layer 60. In various embodiments, for example, the semi-hydrophilic first side layer 50 and semi-hydrophilic second side layer 60 can be formed by combining hydrophilic fibers with hydrophobic fibers and formed into a TABCW material. In various embodiments, the semi-hydrophilic first side layer 50 and the semi-hydrophilic second side layer 60 can be constructed as a multi-layer laminate such as, for example, bonding a top layer formed of a spunbond material to a bottom layer formed of a film material. Each of the first side layer 50 and the second side layer 60 can be in an overlapping configuration with the central layer 40 providing the topsheet layer 20 with a first region of overlap 70 and a second region of overlap 80, each region of overlap, 70 and 80, having a width, W2 and W3, respectively, in the transverse direction (T) of at least 10 mm. The semi-hydrophilic first side layer 50 and the semi-hydrophilic second side layer 60 can provide a wearer of the absorbent article 10 with a body-facing surface, 54 and 64, respectively, which can be soft and gentle-to-the-skin while the material properties of each of the semi-hydrophilic first side layer 50 and the semi-hydrophilic second side layer 60 can enable bodily exudates to pass through the semi-hydrophilic first side layer 50 and the semi-hydrophilic second side layer 60 into an interior layer, such as, for example, an absorbent core 30 of the absorbent article 10 and remain associated with the interior layer rather than either maintaining an association with the first side layer 50 and the second side layer 60 or migrating back to the first side layer 50 and second side layer 60 from the interior layer of the absorbent article 10.

As the exposed region 90 of the central layer 40 is less than 40 mm, the inner edge 52 of the first side layer 50 and the inner edge 62 of the second side layer 60 are positioned no greater than 20 mm in the transverse direction (T) from the longitudinal centerline 32 of the absorbent article 10. Such a configuration can provide the absorbent article 10 with a narrow exposed region 90 for capturing bodily exudates directly from the wearer of the absorbent article 10. In various embodiments, for example, the central layer 40 can be formed from a hydrophilic material such as a TABCW or cotton material and each of the first side layer 50 and the second side layer 60 can be formed from a TABCW material or a multi-layer laminate in which a spunbond material is the body-facing layer. In such embodiments, such a combination of materials forming the topsheet layer 20 can provide the wearer of the absorbent article 10 with a soft and gentle-to-the-skin topsheet layer 20 while allowing for intake of the bodily exudates through the narrow exposed region 90 of the central layer 40 and a reduction in the feeling of wetness as each of the semi-hydrophilic side layers, 50 and 60, can reduce the amount of bodily exudates remaining associated with the topsheet layer 20 or migrating from an interior layer of the absorbent article 10, such as the absorbent core 30, back to the topsheet layer 20. In various embodiments, for example, the central layer 40 can be formed from a hydrophilic material such as an aperture polyethylene film which has been treated to be hydrophilic and each of the first side layer 50 and the second side layer 60 can be formed from a TABCW material or a multi-layer laminate in which a spunbond material is the body-facing layer. In such embodiments, the narrow exposed region 90 of the central layer 40 can provide the absorbent article 10 with a smaller region of exposed material which may irritate the skin of the wearer of the absorbent article 10 while each of the first side layer 50 and second side layer 60 can provide the wearer of the absorbent article 10 with soft and gentle-to-the-skin regions of the topsheet layer 20 while allowing for intake of the bodily exudates through the narrow exposed region 90 of the central layer 40 and a reduction in the feeling of wetness as each of the semi-hydrophilic side layers, 50 and 60, can reduce the amount of bodily exudates remaining associated with the topsheet layer 20 or migrating from an interior layer of the absorbent article 10, such as the absorbent core 30, back to the topsheet layer 20.

Absorbent Core:

An absorbent core 30 can be positioned between the topsheet layer 20 and the backsheet layer 22. The absorbent core 30 can generally be any single layer structure or combination of layer components, which can demonstrate some level of compressibility, conformability, be non-irritating to a wearer's skin, and capable of absorbing and retaining liquids and other body exudates. Additionally, the absorbent core 30 can provide additional capacity to absorb and retain body exudates such as menses. In various embodiments, the absorbent core 30 can be formed from a variety of different materials and can contain any number of desired layers. For example, the absorbent core 30 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers.

In various embodiments, if desired, the absorbent core 30 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly(vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 30 in any amount as desired.

Regardless of the combination of absorbent materials used in the absorbent core 30, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

The shape of the absorbent core 30 can vary as desired and can comprise any one of various shapes including, but not limited to, triangular, rectangular, dog-bone and elliptical shapes. In various embodiments, the absorbent core 30 can have a shape that generally corresponds with the overall shape of the absorbent article 10. The dimensions of the absorbent core 30 can be substantially similar to those of the absorbent article 10, however, it will be appreciated that the dimensions of the absorbent core 30 while similar, will often be less than those of the overall absorbent article 10, in order to be adequately contained therein.

By way of example, suitable materials and/or structures for the absorbent core 30 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

As described above, in various embodiments, an absorbent core 30 can be a single layer structure and can include, for example, a matrix of cellulosic fluff and superabsorbent material. In various embodiments, an absorbent core 30 can have at least two layers of material, such as, for example, a body facing layer and a garment facing layer. In various embodiments, the two layers can be identical to each other. In various embodiments, the two layers can be different from each other. In such embodiments, the two layers can provide the absorbent article 10 with different absorption properties as deemed suitable. In various embodiments, the body facing layer of the absorbent core 30 may be constructed of an airlaid material and the garment facing layer of the absorbent core 30 may be constructed of a superabsorbent polymer-containing compressed sheet. In such embodiments, the airlaid material can have a basis weight from about 40 to about 200 gsm and the superabsorbent polymer-containing compressed sheet can be a cellulosic fluff based material that can be a combination of cellulosic pulp and SAP enclosed with a tissue carrier and having a basis weight from about 40 to about 400 gsm.

Embossing:

As described herein, the first side layer 50 is positioned into an overlapping configuration with the central layer 40 and forms a first region of overlap 70. Additionally, the second side layer 60 is positioned into an overlapping configuration with the central layer 40 and forms a second region of overlap 80. Each of the first side layer 50 and the second side layer 60 can be bonded to the central layer 40 in each of the first region of overlap 70 and the second region of overlap 80 utilizing an embossing technique. Utilizing an embossing technique to bond each of the first side layer 50 and the second side layer 60 to the central layer 40 can form at least one embossment in each of the first region of overlap 70 and the second region of overlap 80. In addition to bonding the first side layer 50 and the second side layer 60 to the central layer 40, the embossing technique utilized to form each embossment in each of the first region of overlap 70 and the second region of overlap 80 can also compress the material forming the absorbent core 30 thereby forming a depression in the absorbent core 30 underneath the formed embossment in the depth direction (Z) of the absorbent article 10. In various embodiments in which an intervening layer(s) of material is present between the topsheet layer 20 and the absorbent core 30 of the article, the embossing technique utilized to form each embossment in each of the first region of overlap 70 and the second region of overlap 80 can also compress the material of the intervening layer(s) as well as the material of the absorbent core 30 thereby forming a depression in each of the intervening layer(s) and the absorbent core 30 underneath the formed embossment in the depth direction (Z) of the absorbent article 10. Each embossment can, therefore, have a height in the depth direction (Z) of the absorbent article 10 that extends from the body facing surface, 54 and 64, of each of the first side layer 50 and second side layer 60, respectively, and into at least a portion of the absorbent core 30 of the absorbent article 10.

Each embossment formed in the first region of overlap 70 and the second region of overlap 80 provides for a compression of at least a semi-hydrophilic material (the first side layer 50 or the second side layer 60) into a hydrophilic material (the central layer 40) and ultimately into the absorbent core 30 of the absorbent article 10. The compression of such materials into each other can facilitate funneling of bodily exudates away from the topsheet layer 20 and towards and into the absorbent core 30. In various embodiments in which a plurality of embossments are present in each of the first region of overlap 70 and the second region of overlap 80, the embossments can be configured in any aesthetically pleasing pattern, can be positioned symmetrically, or can be positioned asymmetrically within the absorbent article 10. The embossment can, therefore, provide both an aesthetically pleasing appearance and topography to the absorbent article 10 which can direct body exudates to a desired location and prevent leakage and/or pooling of the body exudate around the edge of the absorbent article 10.

The body facing surface 54 of the first side layer 50 within the first region of overlap 70 can have an area measurement calculated when the absorbent article 10 is viewed in a top down view such as illustrated in FIG. 1. For example, in the embodiment of an absorbent article 10 illustrated in FIG. 1, the first region of overlap 70 can be bounded by the first longitudinal direction side edge 44 of the central layer 40, the inner edge 52 of the first side layer 50, a portion of the first transverse direction end edge 12, and a portion of the second transverse direction end edge 14. Each of the borders of the first region of overlap 70 can provide the boundaries by which to calculate the area of the body facing surface 54 of the first side layer 50 within the first region of overlap 70. Similarly, the body facing surface 64 of the second side layer 60 within the second region of overlap 80 can have an area measurement calculated when the absorbent article 10 is viewed in a top down view such as illustrated in FIG. 1. For example, in the embodiment of an absorbent article 10 illustrated in FIG. 1, the second region of overlap 80 can be bounded by the second longitudinal direction side edge 46 of the central layer 40, the inner edge 62 of the second side layer 60, a portion of the first transverse direction end edge 12, and a portion of the second transverse direction end edge 14. Each of the borders of the second region of overlap 80 can provide the boundaries by which to calculate the area of the body facing surface 64 of the second side layer 60 within the second region of overlap 80.

In various embodiments, from about 10, 15, or 20% to about 25, 30, or 35% of the area of the body facing surface 54 of the first side layer 50 within the first region of overlap 70 contains at least one embossment. In various embodiments, from about 10, 15, or 20% to about 25, 30, or 35% of the area of the body facing surface 64 of the second side layer 60 within the second region of overlap 80 contains at least one embossment.

An embossment can be provided with any shape and configuration as deemed suitable. For example, an embossment can be in the shape of a circle, oval, square, rectangle, diamond, or any other geometric shape deemed suitable. An embossment can have any length in the longitudinal direction (L) as deemed suitable and a width in the transverse direction (T) as deemed suitable. In various embodiments, an embossment located within a region of overlap, 70 or 80, may be fully contained by the borders of the respective region of overlap, 70 or 80. In various embodiments, an embossment located within a region of overlap, 70 or 80, may extend beyond a border of the region of overlap, 70 or 80, to connect with a secondary embossment positioned external to the region of overlap, 70 or 80. For example, an embossment within the first region of overlap 70 may be configured to extend beyond the inner edge 52 of the first side layer 50 and connect with a secondary embossment within the exposed region 90 of the absorbent article 10.

The absorbent article 10 can have an anterior region 100, a posterior region 102, and a central region 104 positioned between the anterior region 100 and the posterior region 102. In various embodiments, an embossment can have length in the longitudinal direction (L) such that it extends from the anterior region 100 through the central region 104 and into the posterior region 102 of the absorbent article 10. In various embodiments, each of the regions of overlap, 70 and 80, can have a plurality of embossments and each embossment can be discrete and disconnected from each other embossment.

In various embodiments, an embossment is positioned only within the anterior region 100. In various embodiments, an embossment is positioned only within the central region 104. In various embodiments, an embossment is positioned only within the posterior region 102. In various embodiments, an embossment is positioned within each of the anterior region 100 and central region 104. In various embodiments, an embossment is positioned within each of the central region 104 and posterior region 102. In various embodiments, each region of overlap, 70 and 80, can have a plurality of embossments and the plurality of embossments can be evenly distributed throughout the area of the body facing surfaces, 54 and 64, of each of the regions of overlap, 70 and 80, respectively. In various embodiments, each region of overlap, 70 and 80, can have a plurality of embossments and the central region 104 of the absorbent article 10 can have a greater concentration of the plurality of embossments than either of the anterior region 100 or the posterior region 102 of the absorbent article 10. In various embodiments, each region of overlap, 70 and 80, can have a plurality of embossments such as a first embossment having a length in the longitudinal direction (L) extending from the anterior region 100 through the central region 104 and into the posterior region 102 as well as multiple discrete embossments which are concentrated in the central region 104 of each of the first region of overlap 70 and second region of overlap 80. In various embodiments, each region of overlap, 70 and 80, can have a plurality of embossments such as a first embossment having a length in the longitudinal direction (L) extending from the anterior region 100 through the central region 104 and into the posterior region 102 as well as multiple discrete embossments which can be evenly distributed throughout each of the anterior region 100, posterior region 102, and central region 104 of each of the first region of overlap 70 and the second region of overlap 80.

Suitable embossing techniques include, for example, the use of raised elements to impart the desired embossing pattern to create a compression, an embossment, in the layers of the absorbent article 10. For instance, a suitable process may include using thermal bonding wherein the absorbent article 10 is passed through two rolls (e.g., steel, rubber, etc.) where one is engraved with an embossing pattern and the other is flat. One or both rolls may be heated. In addition, thermal and/or ultrasonic bonding techniques may be employed to create the embossing regions.

Figure 4:
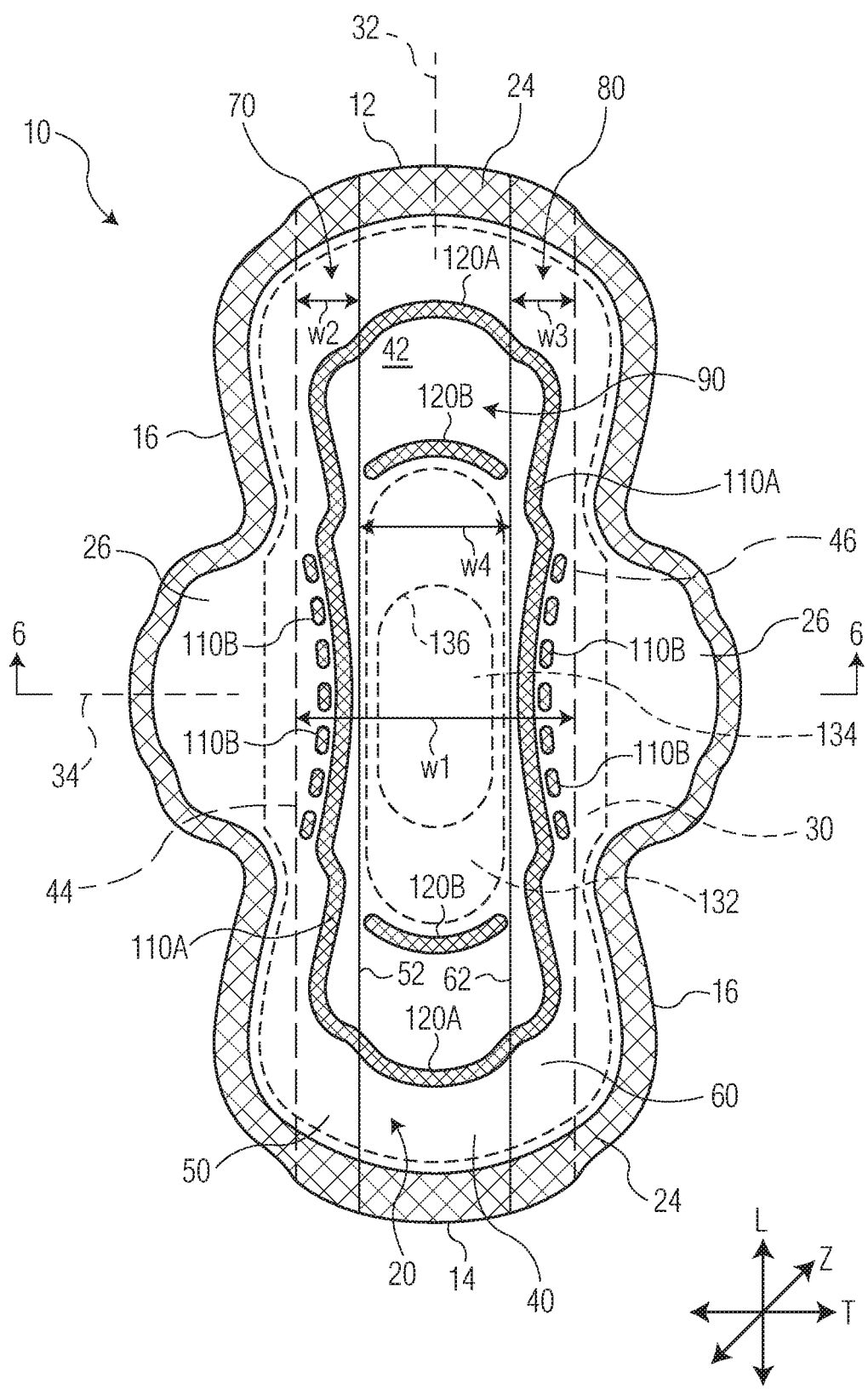
FIG. 4 is a top down view of an embodiment of an absorbent article.
Figure 6:
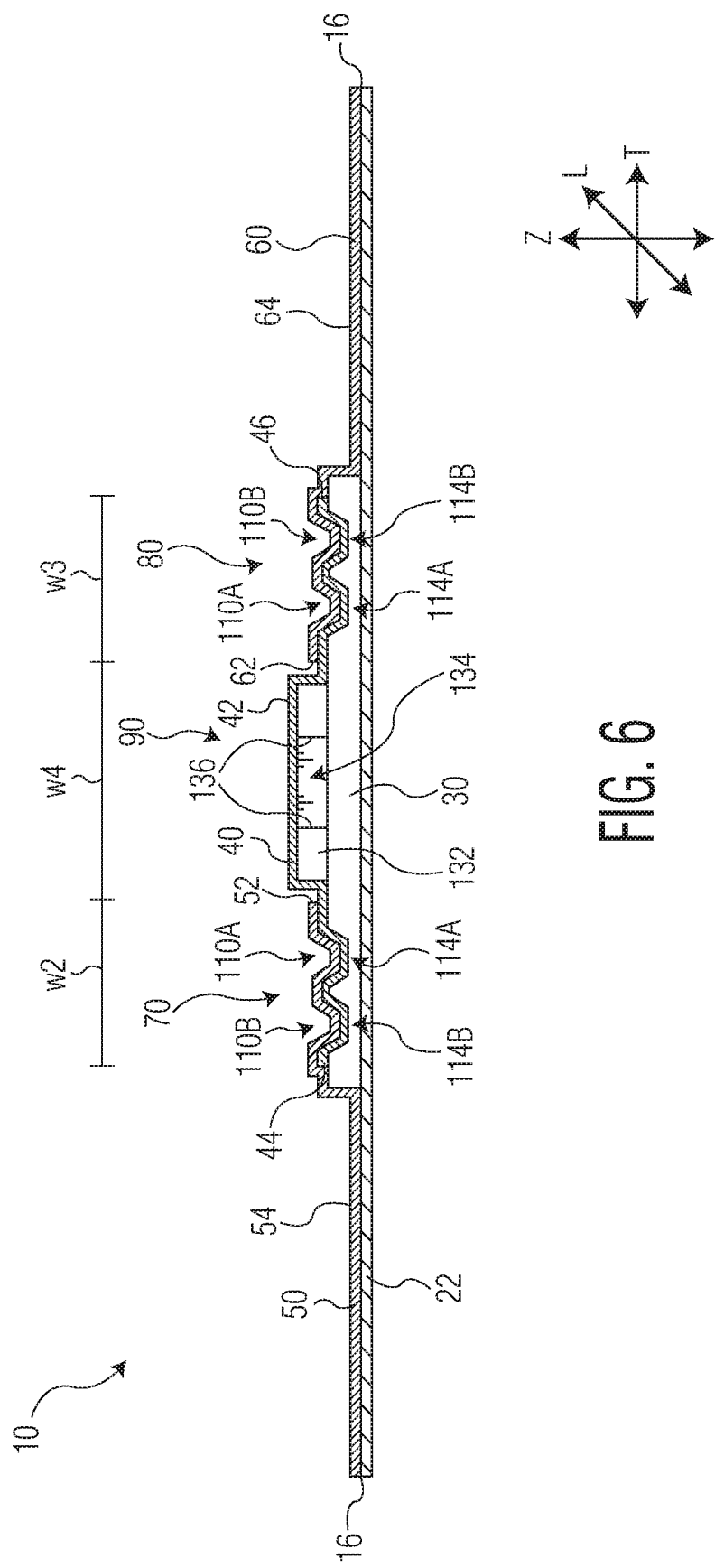
FIG. 6 is a cross-sectional view of the absorbent article of FIG. 4 taken along line 6-6.

Referring to FIGS. 1 and 4, each of the first region of overlap 70 and the second region of overlap 80 can have a plurality of embossments. Each of the first region of overlap 70 and the second region of overlap 80 can have an embossment 110A which can extend generally in the longitudinal direction (L) of the absorbent article 10 and have a longitudinal length such that the embossment 110A can be positioned in each of the anterior region 100, central region 104, and posterior region 102 of each of the first region of overlap 70 and second region of overlap 80. Each of the first region of overlap 70 and the second region of overlap 80 can also have a plurality of discrete embossments 110B which are illustrated in the shape of an oval and which are concentrated in the central region 104 of the absorbent article 10. The embossment 110A of the first region of overlap 70 crosses over the inner edge 52 of the first side layer 50 and into the exposed region 90 in both the anterior region 100 and posterior region 102 of the absorbent article 10 and connects with a secondary embossment 120A in each of the anterior region 100 and posterior region 102 of the absorbent article 10. The embossment 110 of the second region of overlap 80 crosses over the inner edge 62 of the second side layer 60 and into the exposed region 90 in both the anterior region 100 and posterior region 102 of the absorbent article 10 and connects with the same secondary embossment 120A in each of the anterior region 100 and posterior region 102 as is connected to the embossment 110A of the first region of overlap 70. The exposed region 90 can further have a pair of discrete secondary embossments 120B wherein one of the pair of discrete secondary embossments 120B is located in the anterior region 100 and the other of the pair of discrete secondary embossments 120B is located in the posterior region 102 of the absorbent article 10. Referring to FIGS. 3 and 6 which are cross-sectional views of the absorbent articles 10 of FIGS. 1 and 4, respectively, taken along lines 3-3 and 6-6, respectively, at the transverse centerline 34 of each of the absorbent articles 10, it is illustrated that each of the embossments, 110A and 110B, have created depressions, 114A and 114B, into the absorbent core 30 of each of the absorbent articles 10.

Figure 7:
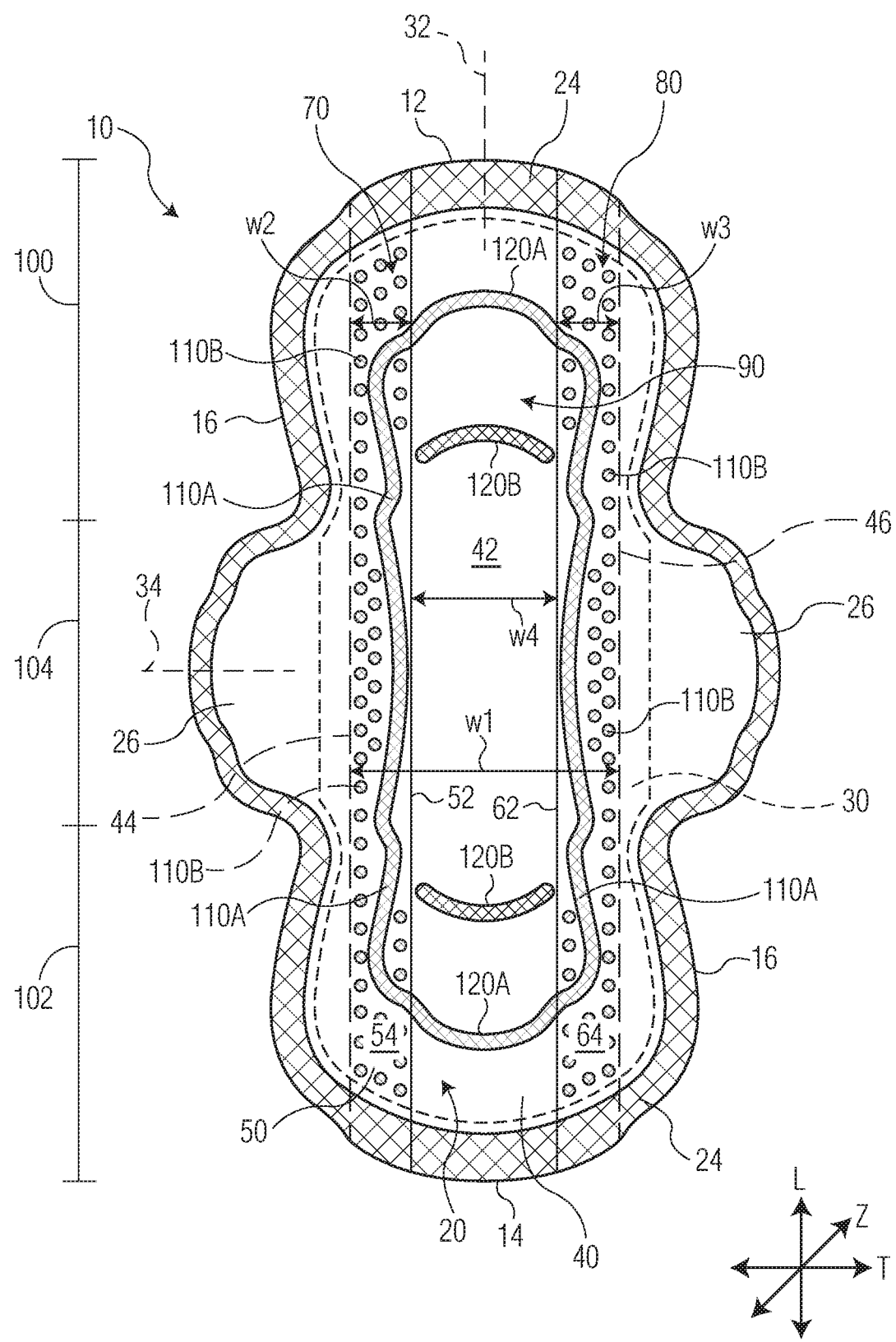
FIG. 7 is a top down view of an embodiment of an absorbent article.
Figure 8:
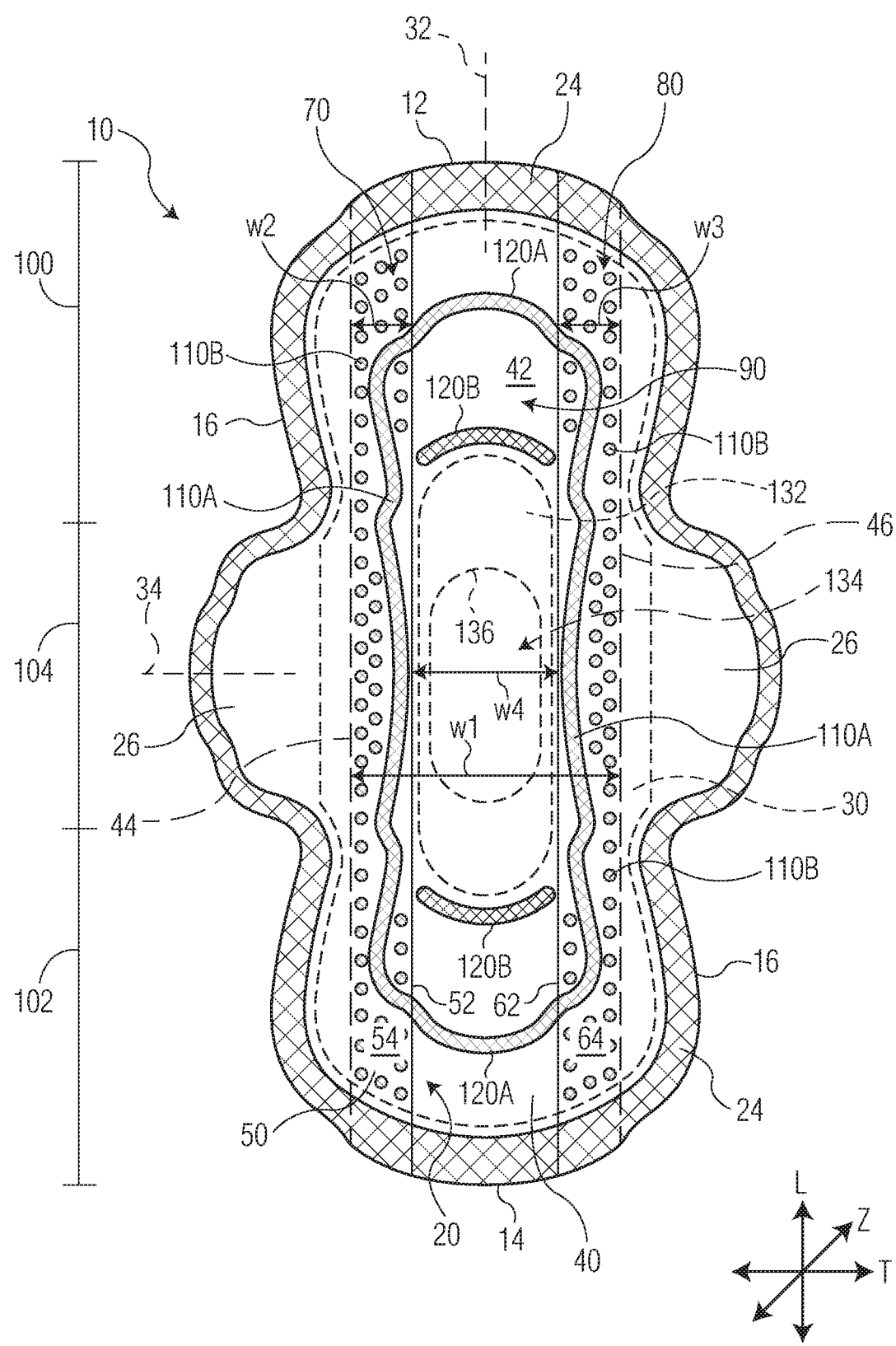
FIG. 8 is a top down view of an embodiment of an absorbent article.

Referring to FIGS. 7 and 8, each of the first region of overlap 70 and the second region of overlap 80 can have a plurality of embossments. Each of the first region of overlap 70 and the second region of overlap 80 can have an embossment 110A which can extend generally in the longitudinal direction (L) of the absorbent article 10 and have a longitudinal length such that the embossment 110A can be positioned in each of the anterior region 100, central region 104, and posterior region 102 of each of the first region of overlap 70 and second region of overlap 80. Each of the first region of overlap 70 and the second region of overlap 80 can also have a plurality of discrete embossments 110B which are illustrated in the shape of a circle and which are evenly distributed throughout the anterior region 100, central region 104, and posterior region 102 of each of the first region of overlap 70 and the second region of overlap 80 of the absorbent article 10. The embossment 110A of the first region of overlap 70 crosses over the inner edge 52 of the first side layer 50 and into the exposed region 90 in both the anterior region 100 and posterior region 102 of the absorbent article 10 and connects with a secondary embossment 120A in each of the anterior region 100 and posterior region 102 of the absorbent article 10. The embossment 110 of the second region of overlap 80 crosses over the inner edge 62 of the second side layer 60 and into the exposed region 90 in both the anterior region 100 and posterior region 102 of the absorbent article 10 and connects with the same secondary embossment 120A in each of the anterior region 100 and posterior region 102 as is connected to the embossment 110A of the first region of overlap 70. The exposed region 90 can further have a pair of discrete secondary embossments 120B wherein one of the pair of discrete secondary embossments 120B is located in the anterior region 100 and the other of the pair of discrete secondary embossments 120B is located in the posterior region 102 of the absorbent article 10.

Backsheet Layer:

The backsheet layer 22 is generally liquid impermeable and is the portion of the absorbent article 10 which faces the garment of the wearer. The backsheet layer 22 can permit the passage of air or vapor out of the absorbent article 10 while still blocking the passage of liquids. Any liquid impermeable material may generally be utilized to form the backsheet layer 22. The backsheet layer 22 can be composed of a single layer or multiple layers, and these one or more layers can themselves comprise similar or different materials. Suitable material that may be utilized can be a microporous polymeric film, such as a polyolefin film of polyethylene or polypropylene, nonwovens and nonwoven laminates, and film/nonwoven laminates. The particular structure and composition of the backsheet layer 22 can be selected from various known films and/or fabrics with the particular material being selected as appropriate to provide the desired level of liquid barrier, strength, abrasion resistance, tactile properties, aesthetics and so forth. In various embodiments, a polyethylene film can be utilized that can have a thickness in the range of from about 0.2 or 0.5 mils to about 3.0 or 5.0 mils. An example of a backsheet layer 22 can be a polyethylene film such as that obtainable from Pliant Corporation, Schaumburg, IL, USA. Another example can include calcium carbonate-filled polypropylene film. In still another embodiment, the backsheet layer 22 can be a hydrophobic nonwoven material with water barrier properties such as a nonwoven laminate, an example of which can be a spunbond, meltblown, meltblown, spunbond, four-layered laminate. The backsheet layer 22 can, therefore, be of a single or multiple layer construction, such as of multiple film layers or laminates of film and nonwoven fibrous layers. Suitable backsheet layers 22 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

Figure 5:
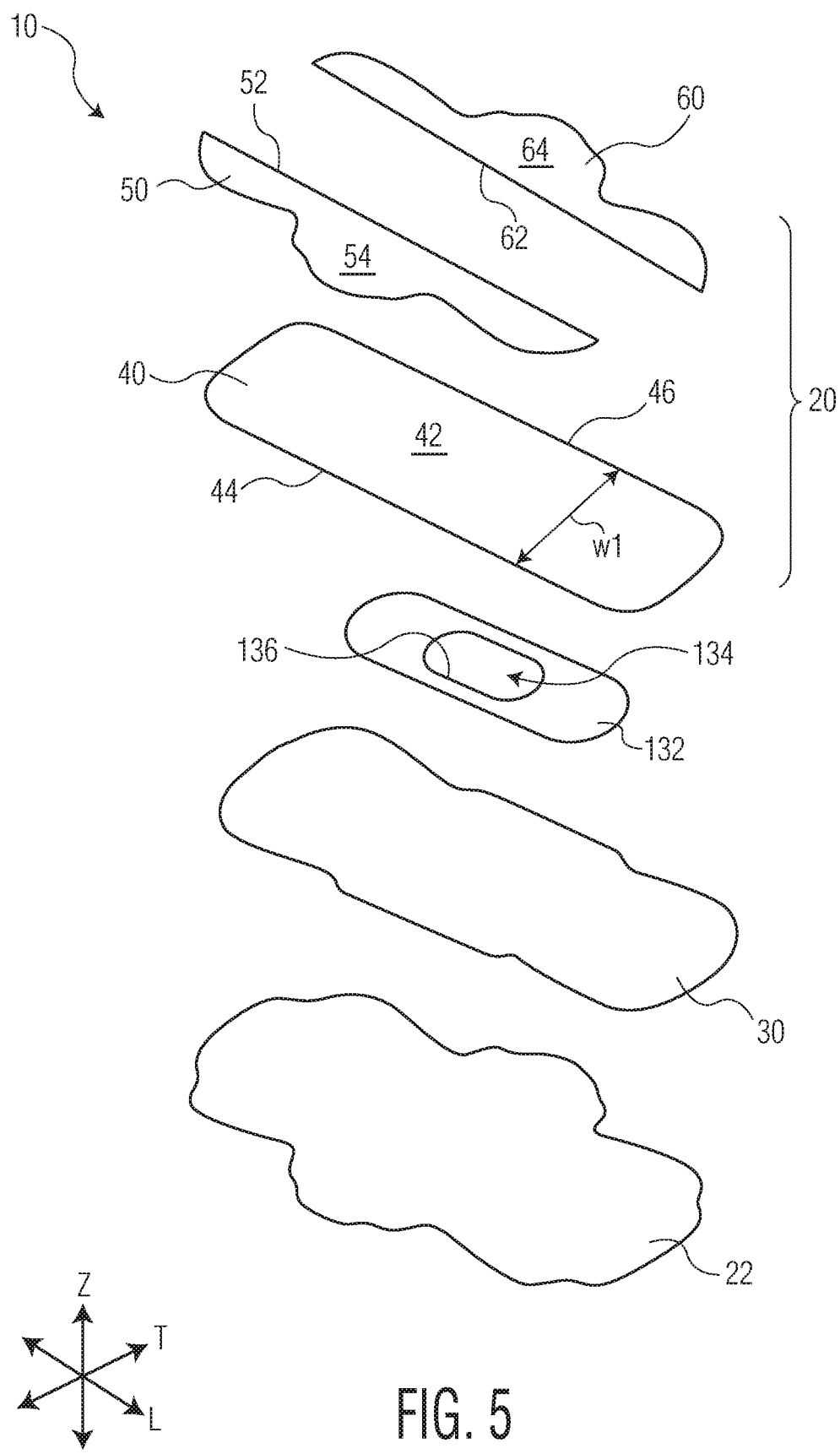
FIG. 5 is an exploded perspective view of the absorbent article of FIG. 4.
Figure 9:
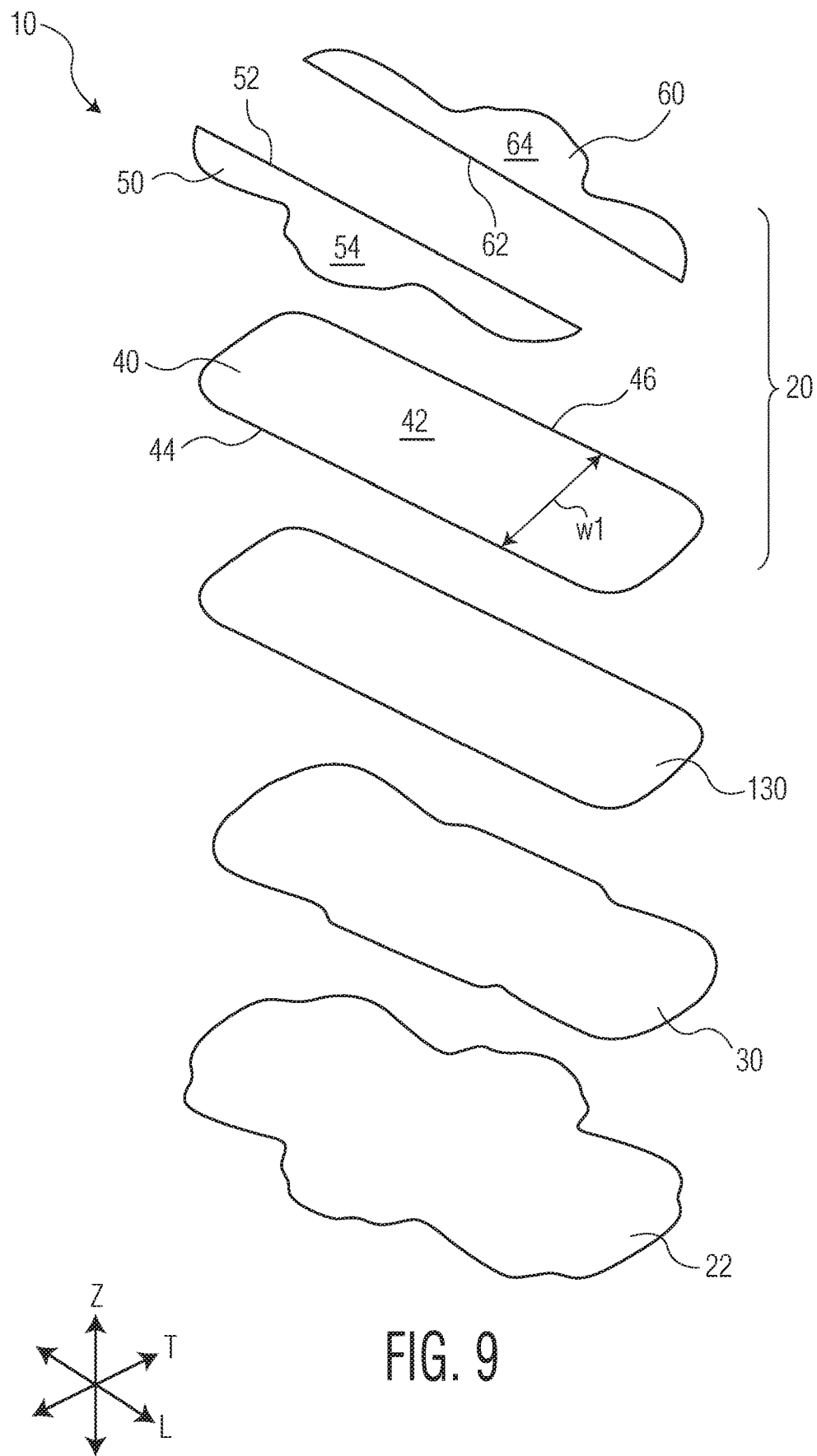
FIG. 9 is an exploded perspective view of an embodiment of an absorbent article.
Figure 10:
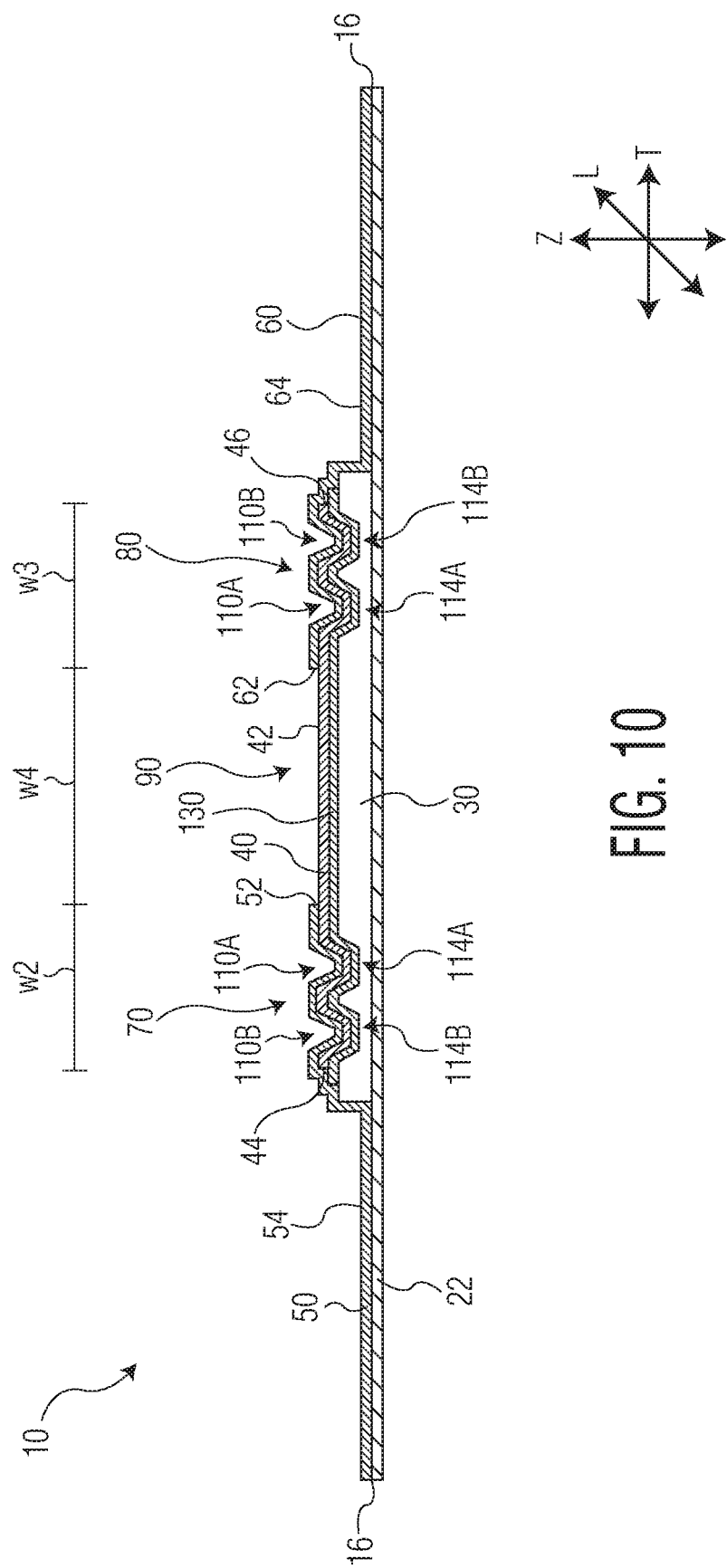
FIG. 10 is a cross-sectional view of the absorbent article of FIG. 9.
Figure 11:
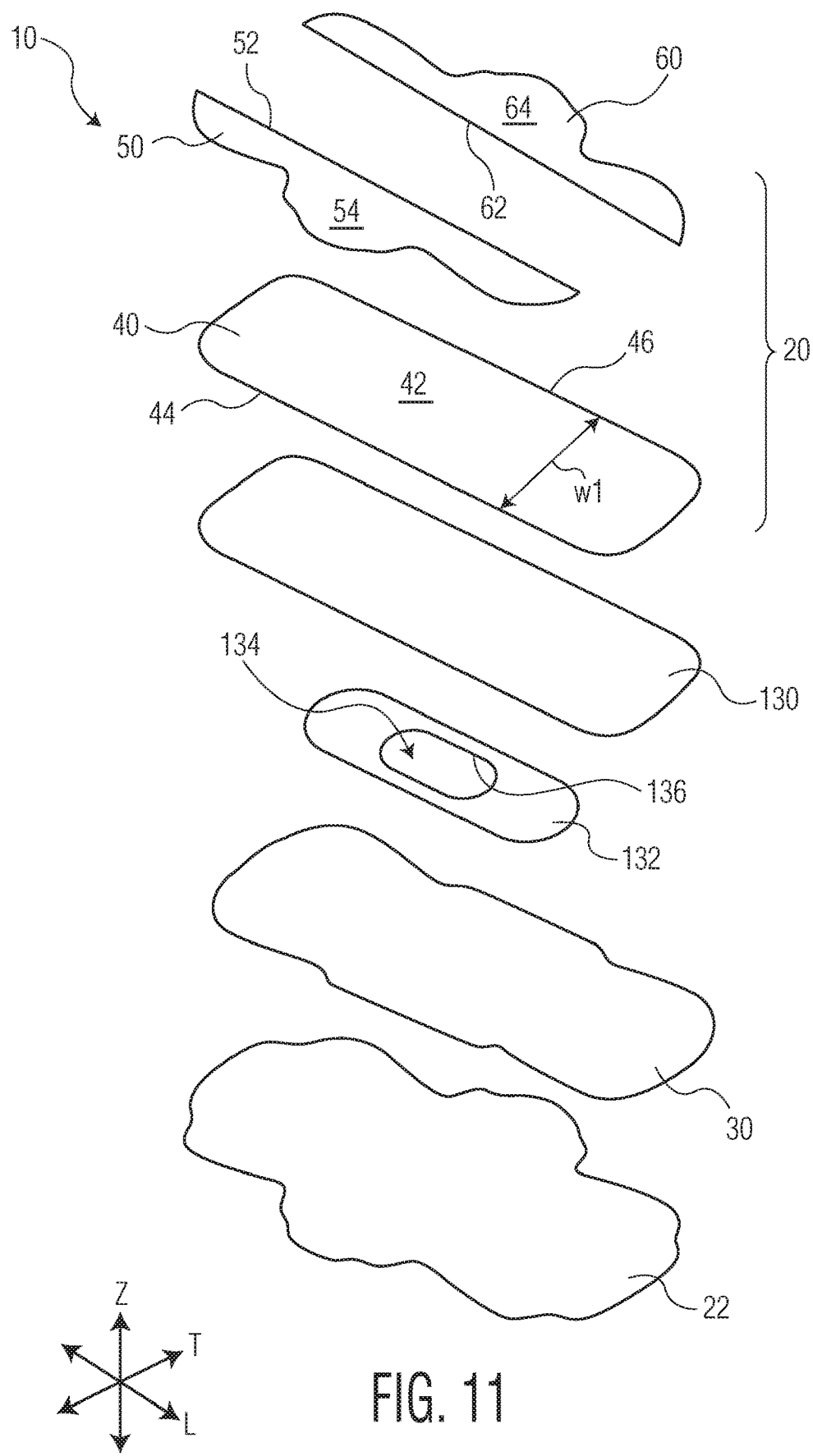
FIG. 11 is an exploded perspective view of an embodiment of an absorbent article.
Figure 12:
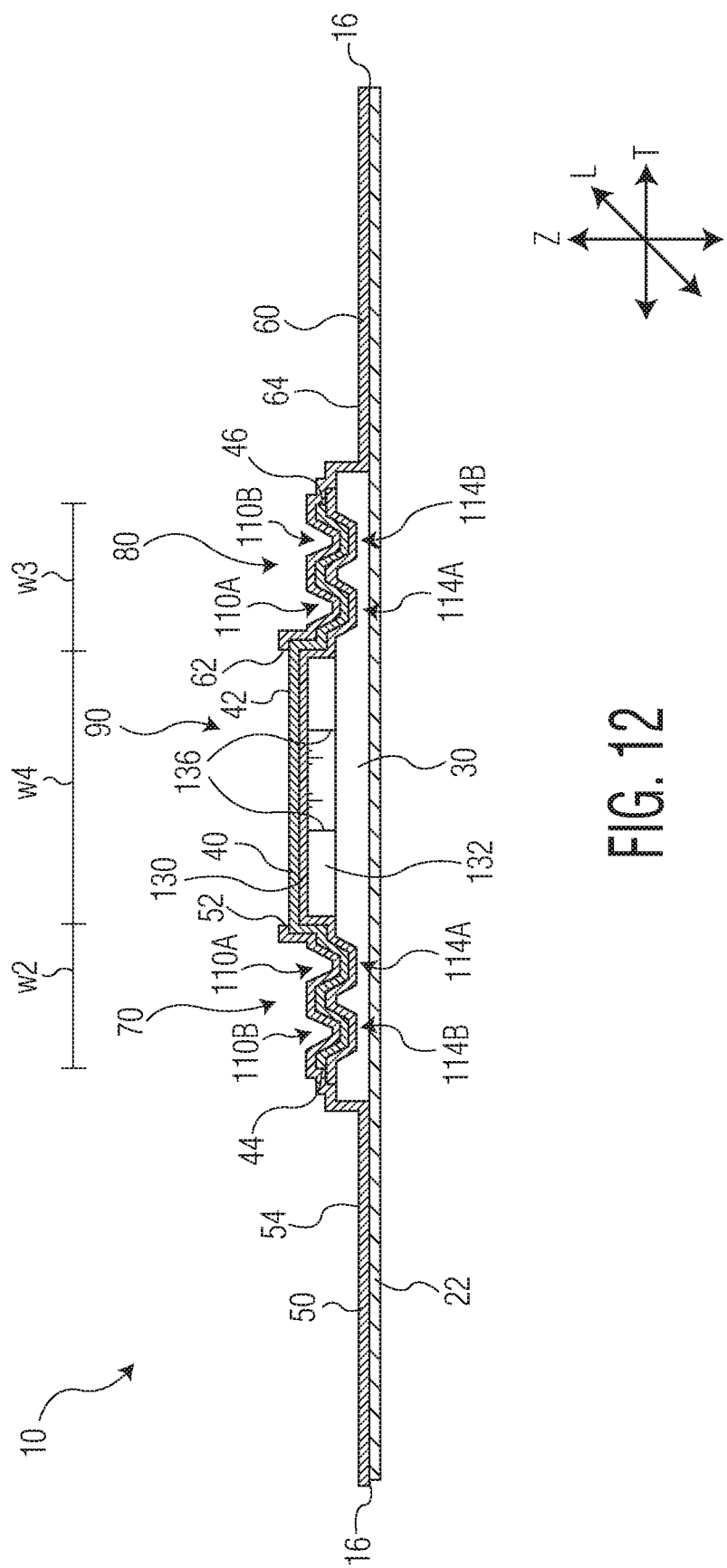
FIG. 12 is a cross-sectional view of the absorbent article of FIG. 11.
Figure 13:
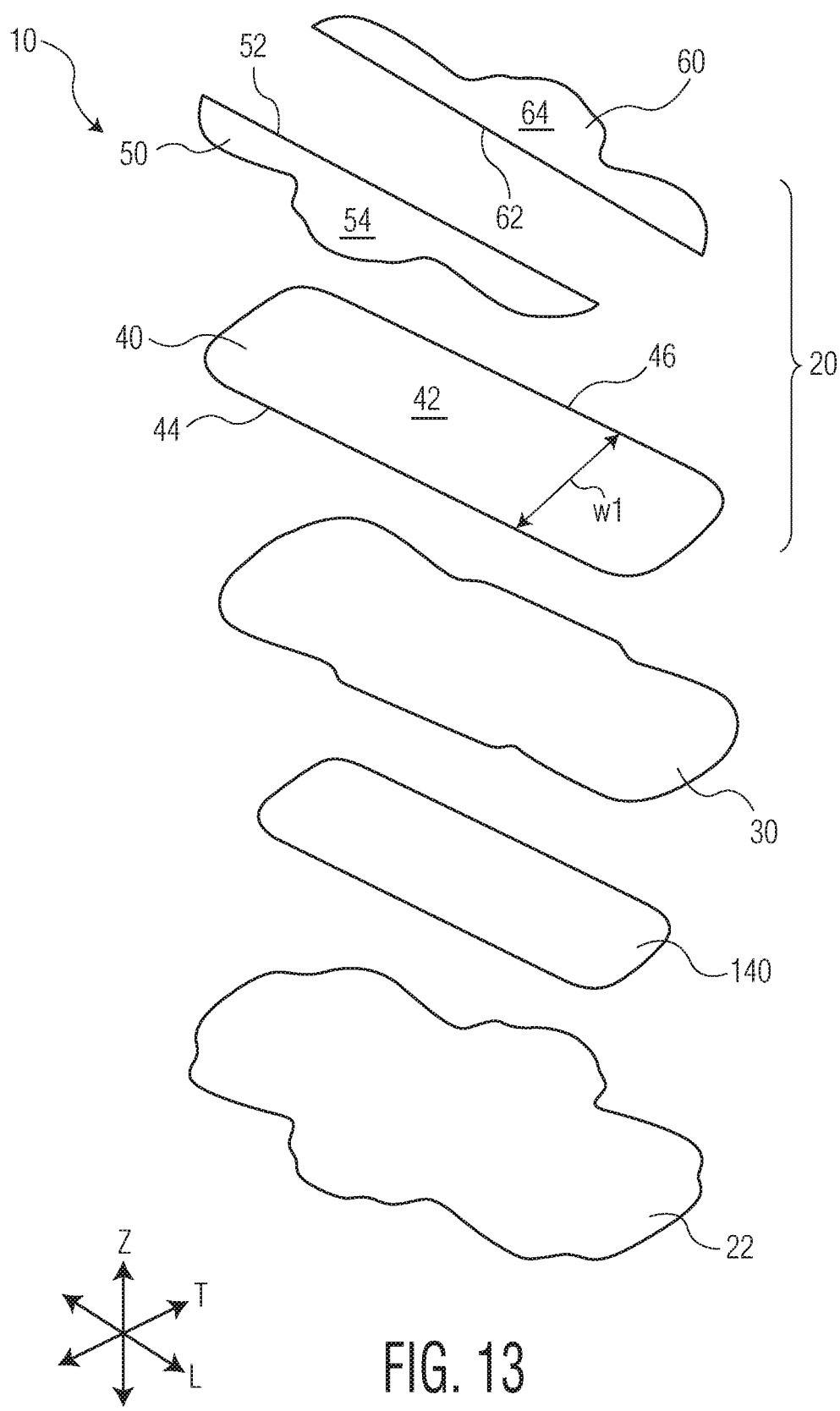
FIG. 13 is an exploded perspective view of an embodiment of an absorbent article.
Figure 14:
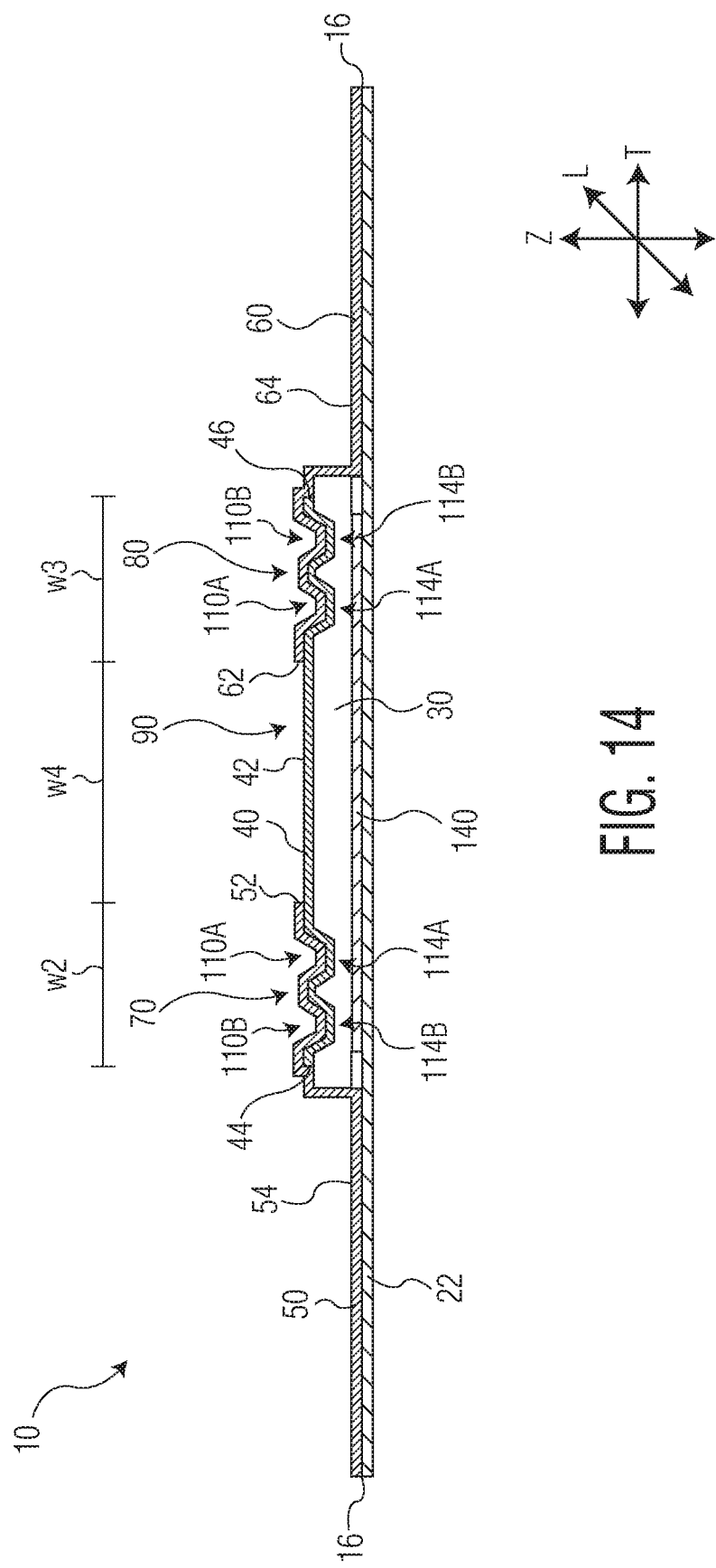
FIG. 14 is a cross-sectional view of the absorbent article of FIG. 13.
Figure 15:
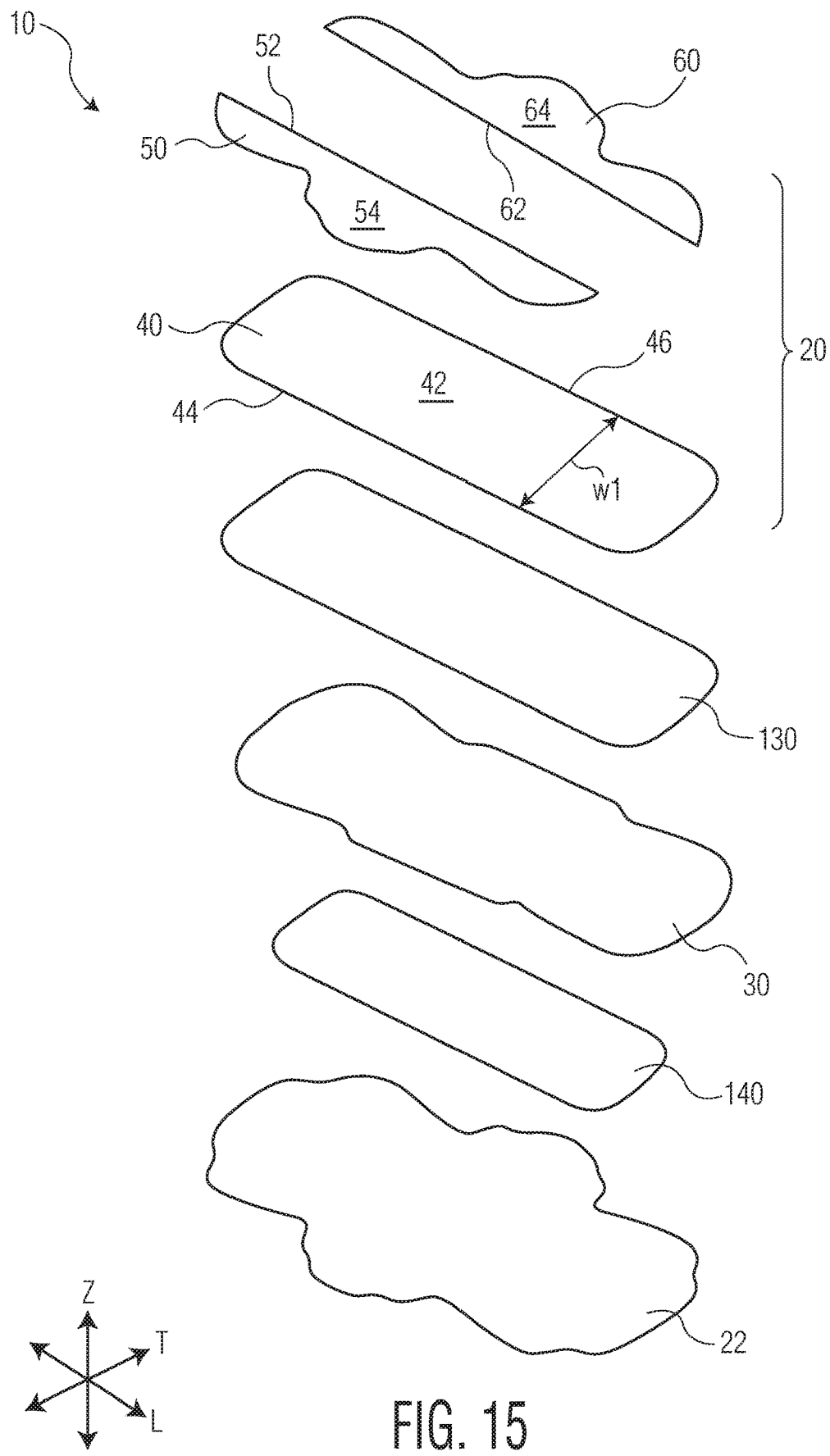
FIG. 15 is an exploded perspective view of an embodiment of an absorbent article.
Figure 16:
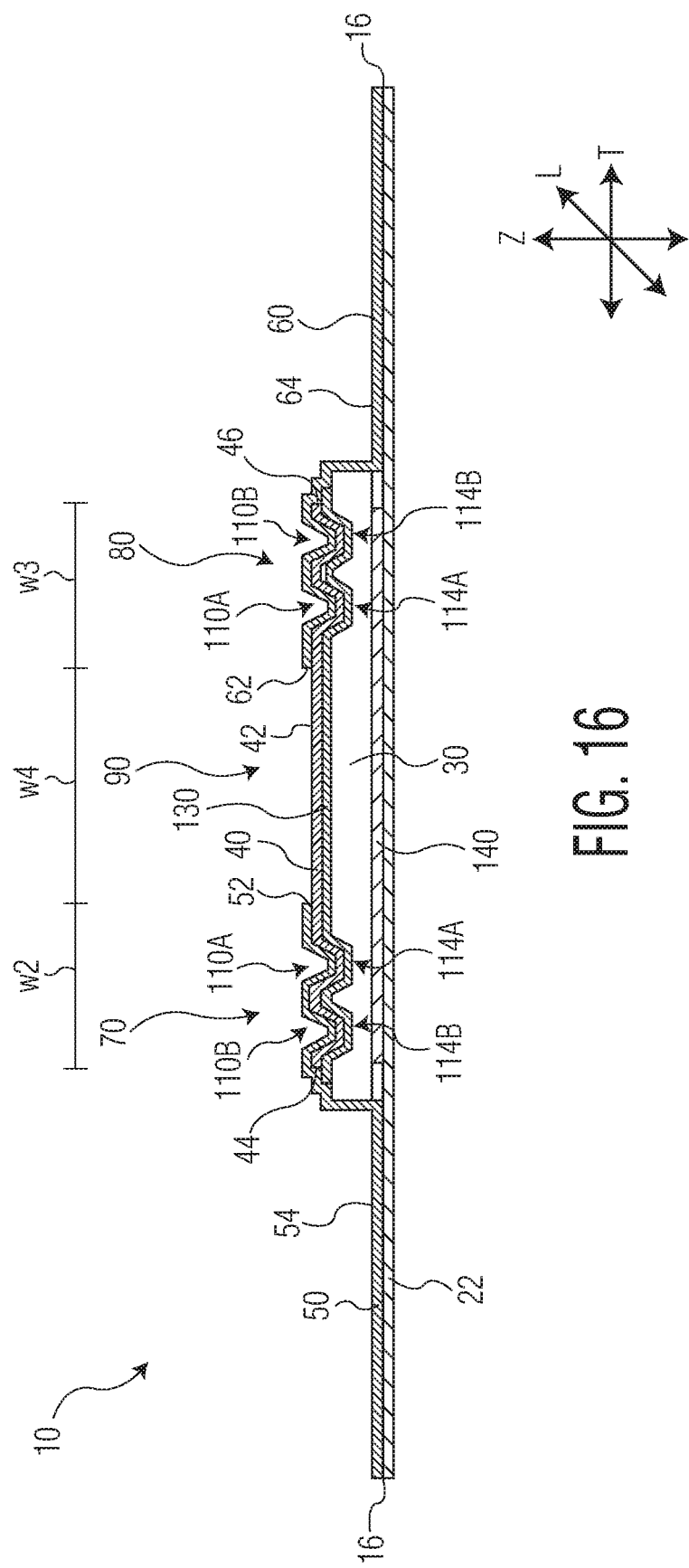
FIG. 16 is a cross-sectional view of the absorbent article of FIG. 15.
Figure 17:
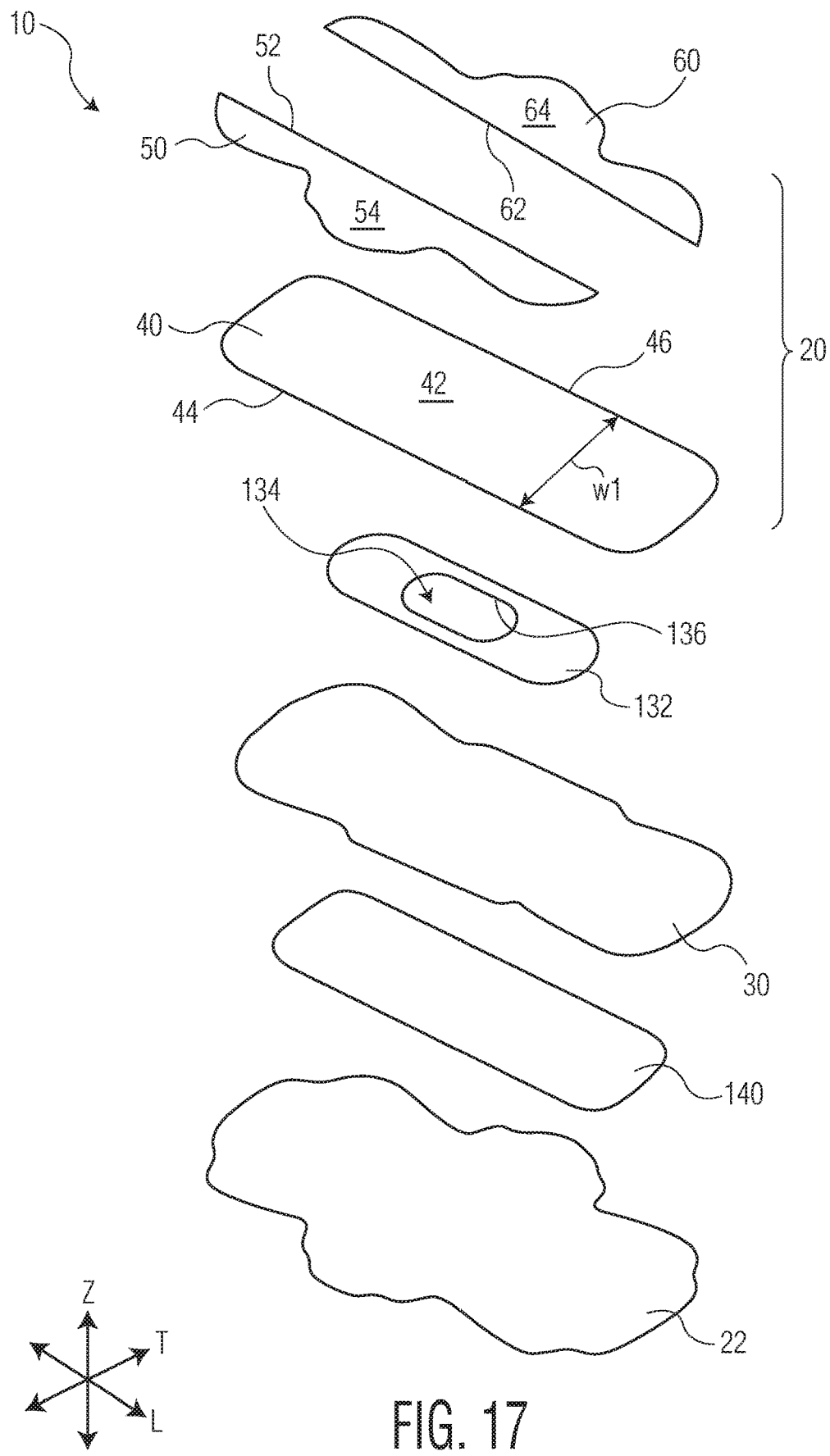
FIG. 17 is an exploded perspective view of an embodiment of an absorbent article.
Figure 18:
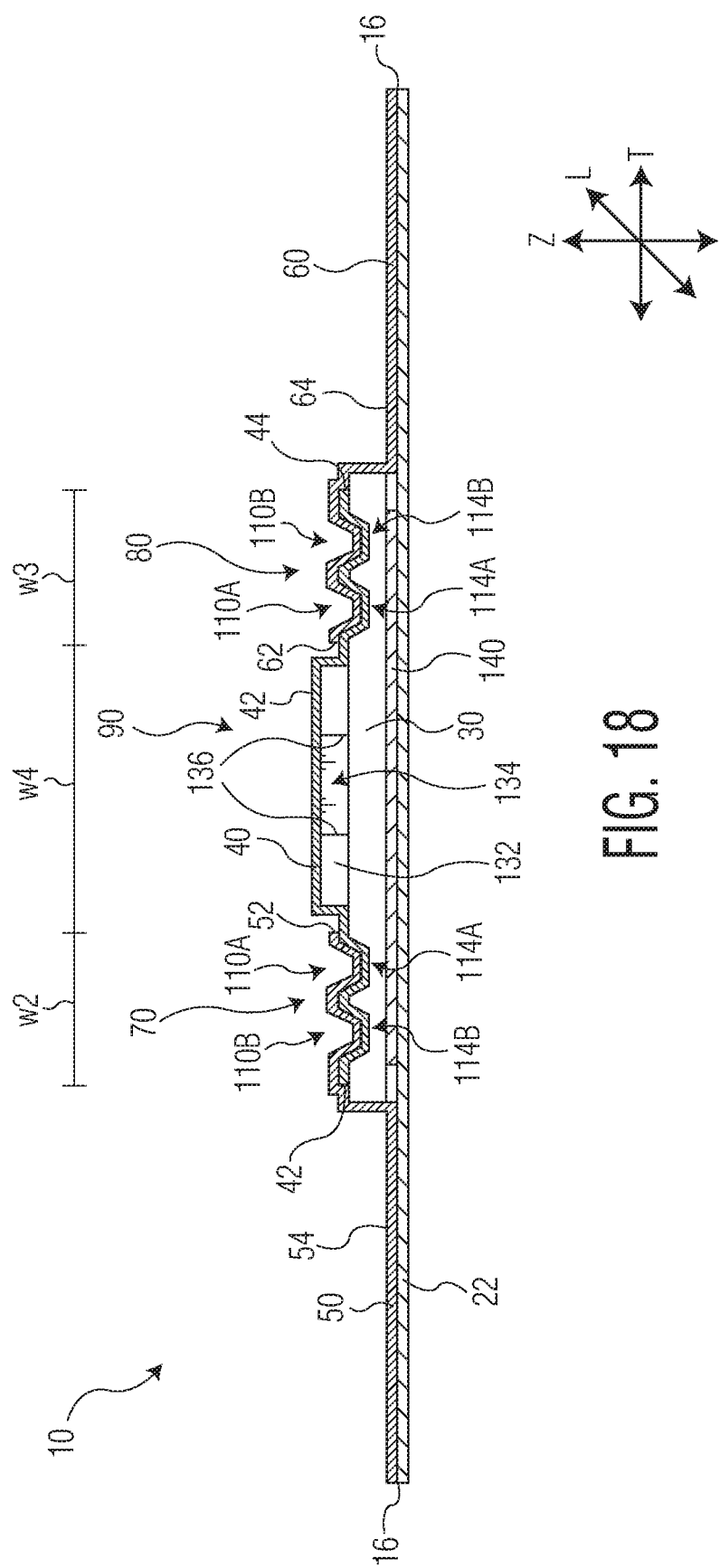
FIG. 18 is a cross-sectional view of the absorbent article of FIG. 17.
Figure 19:
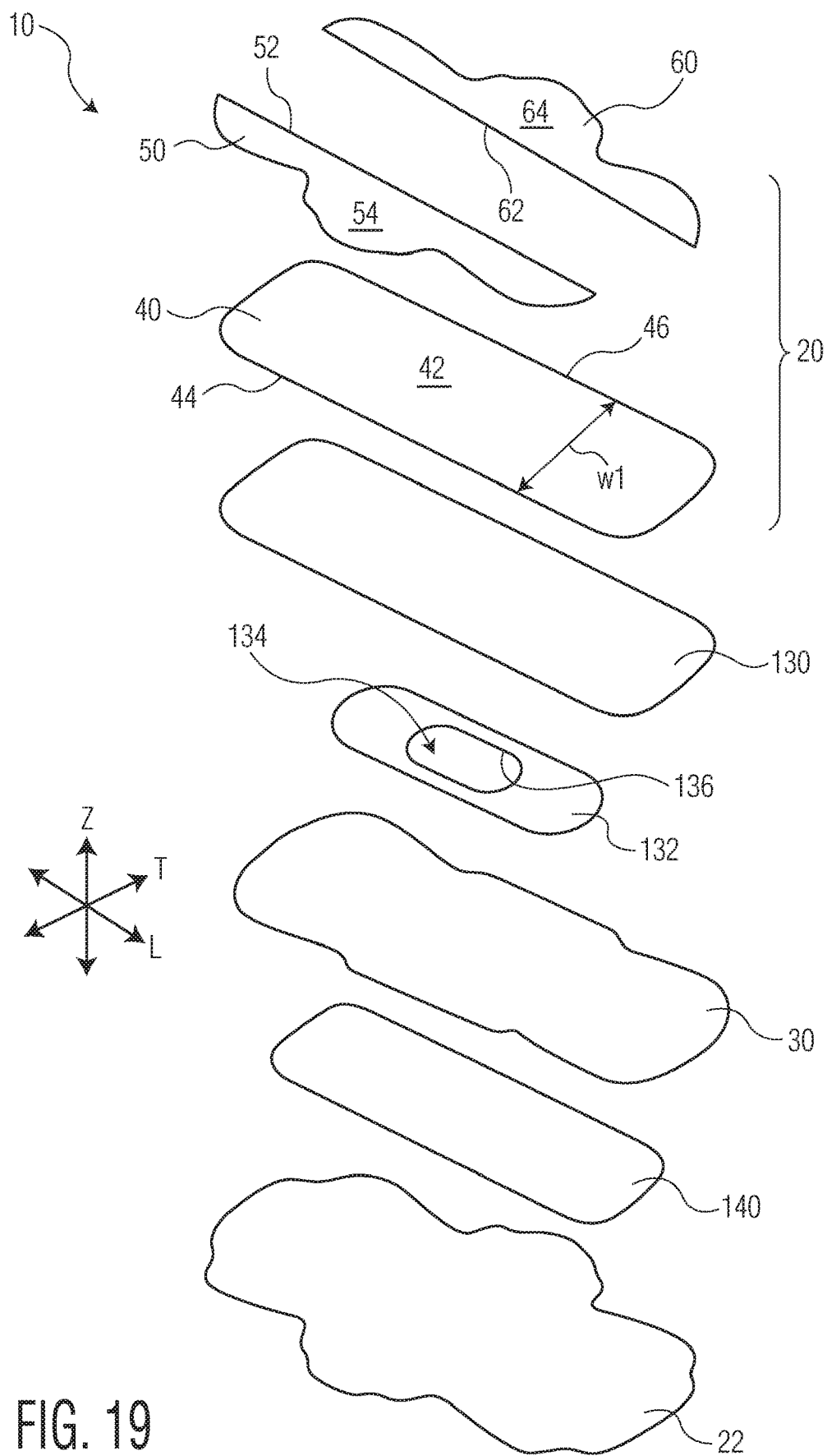
FIG. 19 is an exploded perspective view of an embodiment of an absorbent article.
Figure 20:
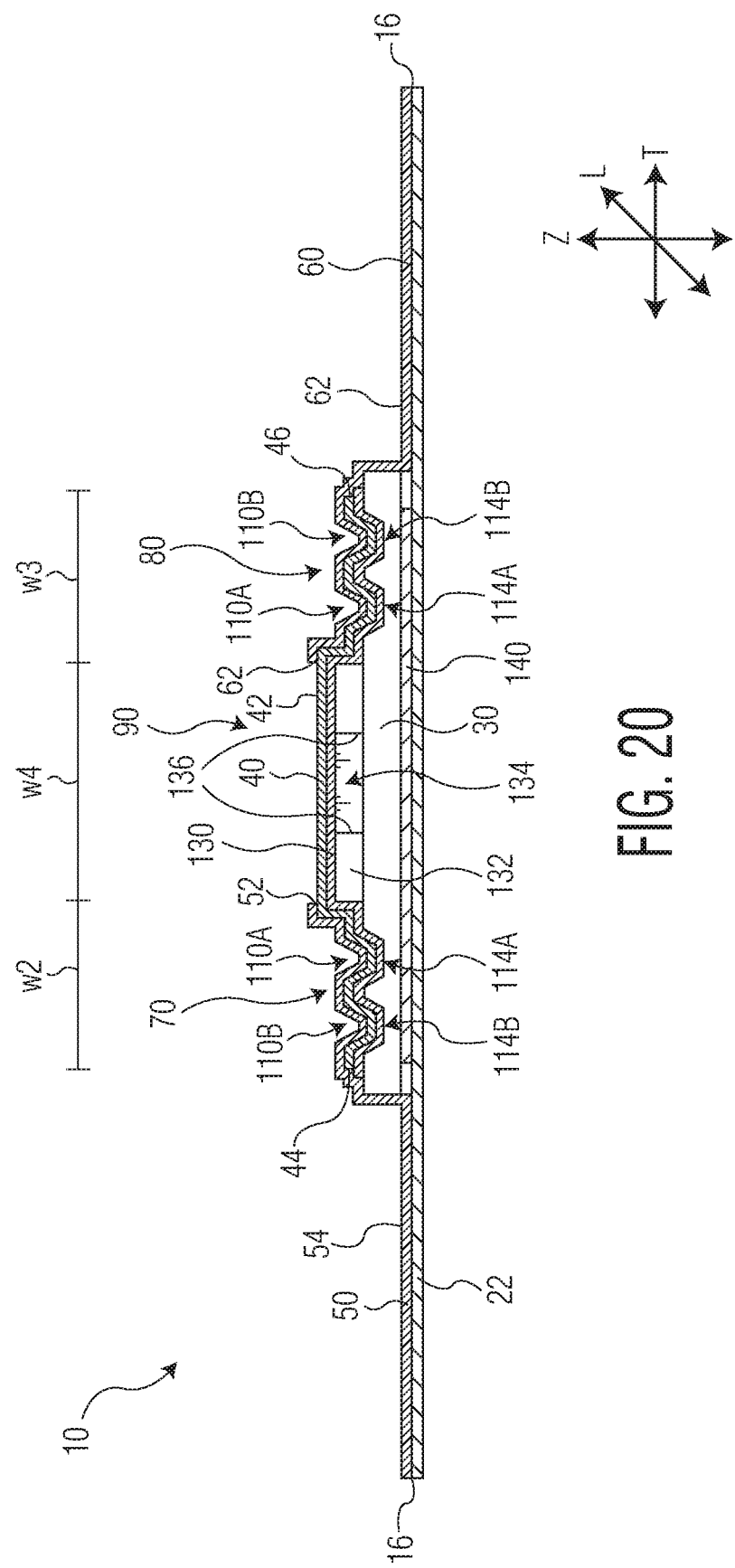
FIG. 20 is a cross-sectional view of the absorbent article of FIG. 19.

Additional Layers:

Referring to FIGS. 4-6 and 8-20, in various embodiments, an absorbent article 10 can optionally include at least one of a surge layer 130 and/or a fluid intake layer 132 and/or a distribution layer 140. FIG. 4 provides an illustration of a top down view of an exemplary embodiment of an absorbent article 10, FIG. 5 provides an illustration of an exploded perspective view of the absorbent article 10 of FIG. 4, and FIG. 6 provides an illustration of a cross-sectional view of the absorbent article 10 of FIG. 4 taken along line 6-6. FIG. 8 provides an illustration of a top down view of an embodiment of an absorbent article 10. FIG. 9 provides an illustration of an exploded perspective view of an embodiment of an absorbent article 10 and FIG. 10 provides a cross-sectional view of the absorbent article of FIG. 9 taken along the transverse centerline. FIG. 11 provides an illustration of an exploded perspective view of an embodiment of an absorbent article 10 and FIG. 12 provides a cross-sectional view of the absorbent article of FIG. 11 taken along the transverse centerline. FIG. 13 provides an illustration of an exploded perspective view of an embodiment of an absorbent article 10 and FIG. 14 provides a cross-sectional view of the absorbent article of FIG. 13 taken along the transverse centerline. FIG. 15 provides an illustration of an exploded perspective view of an embodiment of an absorbent article 10 and FIG. 16 provides a cross-sectional view of the absorbent article of FIG. 15 taken along the transverse centerline. FIG. 17 provides an illustration of an exploded perspective view of an embodiment of an absorbent article 10 and FIG. 18 provides a cross-sectional view of the absorbent article of FIG. 17 taken along the transverse centerline. FIG. 19 provides an illustration of an exploded perspective view of an embodiment of an absorbent article 10 and FIG. 20 provides a cross-sectional view of the absorbent article of FIG. 19 taken along the transverse centerline.

In various embodiments, an absorbent article 10 can include a surge layer 130, such as illustrated, for example, in FIGS. 9 and 10. In various embodiments, an absorbent article 10 can include a fluid intake layer 132, such as illustrated, for example, in FIGS. 4-6, and 8. In various embodiments, an absorbent article 10 can include a distribution layer 140, such as illustrated, for example, in FIGS. 13 and 14. In various embodiments, an absorbent article 10 can include a surge layer 130 and a fluid intake layer 132, such as illustrated, for example, in FIGS. 11 and 12. In various embodiments, an absorbent article 10 can include a surge layer 130 and a distribution layer 140, such as illustrated, for example, in FIGS. 15 and 16. In various embodiments, an absorbent article 10 can include a fluid intake layer 132 and a distribution layer 140, such as illustrated, for example, in FIGS. 17 and 18. In various embodiments, an absorbent article 10 can include a surge layer 130, fluid intake layer 132, and a distribution layer 140, such as illustrated, for example, in FIGS. 19 and 20.

Surge Layer:

An additional layer in the absorbent article 10 can be a surge layer 130. A surge layer 130 can be constructed of any woven or nonwoven material that is easily penetrated by body exudates. The surge layer 130 can help to absorb, decelerate, and diffuse surges or gushes of liquid that may be rapidly introduced into the absorbent article 10. The surge layer 130 can rapidly accept and temporarily hold the liquid prior to releasing the liquid into, for instance, a fluid intake layer 140 and/or absorbent core 30 or any other layer of the absorbent article 10. Various woven fabrics and nonwoven webs can be used to construct the surge layer 130. For example, the surge layer 130 can comprise a nonwoven fabric layer composed of a meltblown or spunbond web of polyolefin or polyester filaments. Such nonwoven fabric layers may include conjugate, biconstituent and homopolymer fibers of staple or other lengths and mixtures of such fibers with other types of fibers. The surge layer 130 can also be a bonded card web or an airlaid web composed of natural and/or synthetic fibers. The bonded carded web may, for example, be a powder bonded carded web, an infrared bonded carded web, or a through air bonded carded web. The bonded carded webs can optionally include a mixture or blend of different fibers. The surge layer 130 typically has a basis weight of less than about 100 gsm, and in some embodiments, from about 10 gsm to about 40 gsm.

The surge layer 130 can be incorporated into the absorbent article 10 in any suitable size and shape based upon the need of the particular absorbent article 10 in which the surge layer 130 is being used. In various embodiments, the surge layer 130 can extend across the entire absorbent article 10 in the longitudinal direction and transverse direction, such that the surge layer 130 can have the same dimensions as the topsheet layer 20. In various embodiments, the surge layer 130 can have a smaller overall length in the longitudinal direction and a smaller overall width in the transverse direction than the topsheet layer 20. In various embodiments, the overall length of the surge layer 130 can be from about 30, 40 or 50% to about 98, 99 or 100% of the overall length of the topsheet layer 20. In various embodiments, the overall width of the surge layer 130 can be from about 10, 25 or 50% to about 98, 99 or 100% of the overall width of the topsheet layer 20.

Fluid Intake Layer:

In various embodiments, the absorbent article 10 can include a liquid permeable fluid intake layer 132 positioned between the topsheet layer 20 and the absorbent core 30. Such a fluid intake layer 132 can be made of a material that can be capable of rapidly transferring, in the Z-direction, body exudates that are delivered to the topsheet layer 20. The fluid intake layer 132 can generally have any shape and/or size desired. In an embodiment, the fluid intake layer 132 can have a curved rectangular shape, with a length equal to or less than the overall length of the absorbent article 10, and a width less than the width of the absorbent article 10. For example, the fluid intake layer 132 can have a length of between about 20, 40 or 60 mm to about 150, 150, 175, 200 or 300 mm and a width of between about 10, 15 or 20 mm to about 60, 80 or 100 mm may be utilized. The fluid intake layer 132 can have a thickness in the depth direction from about 0.5 mm to about 3 mm. Any of a variety of different materials can be capable of being used for the fluid intake layer 132 to accomplish the above-mentioned functions. The material may be synthetic, cellulosic, or a combination of synthetic and cellulosic materials. The fluid intake layer 132 can be constructed from any woven or nonwoven material. For example, the fluid intake layer 132 can be constructed as an airlaid or TABCW material. For example, airlaid cellulosic tissues may be suitable for use in the fluid intake layer 132. The airlaid cellulosic tissue may have a basis weight ranging from about 10 or 100 gsm to about 250 or 300 gsm. The airlaid cellulosic tissue can be formed from hardwood and/or softwood fibers. An airlaid cellulosic tissue can have a fine pore structure and can provide an excellent wicking capacity, especially for menses.

Additionally, to further enhance the ability of the absorbent article 10 to transfer body exudates in the depth (Z) direction from the topsheet layer 20 toward any lower layers in the absorbent article 10 as well as to enhance the ability of the fluid intake layer 132 to conform to the wearer's body based on its ability to bend, the fluid intake layer 132 can have a fluid intake layer opening 134 which can be any suitable shape, such as ovular, circular, rectangular, square, triangular, etc. In various embodiments, the fluid intake layer opening 134 can be elongate and can be oriented in the longitudinal direction of the absorbent article 10. The fluid intake layer opening 134 can be bounded by a perimeter 136 which can form an inner border or inner edge of the fluid intake layer 132.

The fluid intake layer opening 134 can be located at various positions along the longitudinal and transverse directions of the fluid intake layer 132 depending upon the primary location of body exudate intake or the purpose for which the absorbent article 10 is being used. For example, in various embodiments, the fluid intake layer 132 and the fluid intake layer opening 134 can be positioned so that it is in substantial alignment with the longitudinal centerline 32 and the transverse centerline 34 of the absorbent article 10. This allows the fluid intake layer opening 134 to be centrally disposed so that it can be positioned below the main point of body exudate discharge and so that it can act as the primary body exudate receiving area for the absorbent article 10.

However, centralized positioning of the fluid intake layer 132 and the fluid intake layer opening 134 is not required, and in various embodiments, depending on the primary location where body exudate intake might occur, the fluid intake layer 132 and the fluid intake layer opening 134 may be substantially aligned with the longitudinal centerline 32 only. Thus, in various embodiments, the fluid intake layer 132 and the fluid intake layer opening 134 may be shifted in the longitudinal direction towards either transverse direction end edge, 12 or 14, of the absorbent article 10, so that the fluid intake layer opening 134 is not in substantial alignment with the transverse centerline 34.

The fluid intake layer opening 134 can have a longitudinal length from about 15, 20, 30 or 50 mm to about 60, 75, 100 or 150 mm and can have a transverse width from about 10, 15, 20 or 30 mm to about 40, 60 or 80 mm. The fluid intake layer opening 134 can be defined by the perimeter 136 and can have a longitudinal length that is from about 15, 20 or 25% to about 70, 75, or 80% of the overall longitudinal length of the fluid intake layer 132 in the longitudinal direction. The fluid intake layer opening 134 can be defined by the perimeter 136 and can have a transverse width that can be from about 20, 25 or 30% to about 70, 75 or 80% of the overall width of the fluid intake layer 132 in the transverse direction. The fluid intake layer opening 134 can serve to funnel and direct body exudates from the topsheet layer 20 and towards lower layers of the absorbent article 10 in the depth (Z) direction. The fluid intake layer opening 134 can also form a cup or well-like structure for holding body exudates and preventing its leakage away from a central region of the absorbent article 10 and towards the edges of the absorbent article 10.

Distribution Layer:

In various embodiments, the absorbent article 10 can have a distribution layer 140 positioned below the absorbent core 30. The distribution layer 140 can increase absorbency of the absorbent article 10. The distribution layer 140 can be constructed of various materials such as, but not limited to, hydroentangled webs, through air bonded carded webs, meltblown webs, and meltblown microfiber webs. The distribution layer 140 can include a hydrophilic material. The distribution layer 140 can be smaller in size than the absorbent core 30 of the absorbent article 10.

In various embodiments, the distribution layer 140 can have a longitudinal length from about 80, 90, 100, 110, 120, 125 or 130 mm to about 135, 140, 150, 160, 170, 180 or 190 mm and can have a transverse width from about 20, 30, 35 or 40 mm to about 45, 50, 55 or 60 mm. In various embodiments, the distribution layer can have a density of greater than about 0.1 grams per cubic centimeter. The density can be calculated utilizing the formula: density=basis weight (gsm)/thickness (mm)/1000. In various embodiments, the distribution layer 40 can have a basis weight from about 10, 20, 25, 30 or 50 gsm to about 60, 70, 80, 90, 100, 120, 140, 150, 160, 180 or 200 gsm.

In various embodiments, the distribution layer 140 can be a hydroentangled web. The hydroentangled web can include a hydroentangled spunbond material and a pulp material. The hydroentangled spunbond material can include a polypropylene material. The spunbond material can be present in an amount from about 10% or 15% to about 20% or 25% of the hydroentangled web. The pulp material can be present in an amount from about 75% or 80% to about 85%, 90% or 100% of the hydroentangled web. The hydroentangled web can have a basis weight from about 30 or 60 gsm to about 90, 200, or 300 gsm. Without being bound by theory, it is believed that a higher basis weight hydroentangled web can improve the absorbency of the distribution layer 140. It is further believed that an improved absorbency of the distribution layer 140 can further result in an improved fluid retention capacity of the absorbent article 10. The basis weight of the hydroentangled web can be balanced with the desired flexibility of the absorbent article 10. In various embodiments, the distribution layer 140 can be a pulp sheet material. In such embodiments, the distribution layer 140 can contain 100% pulp material. In such embodiments, the distribution layer 140 can have a basis weight from about 30 or 60 gsm to about 90, 200 or 300 gsm. In various embodiments, the distribution layer 140 can include a bicomponent fluid distribution layer, which can increase absorbency by providing a high void space and may be made of a through air bonded carded web, having a basis weight, in an embodiment, of between about 25 gsm and 100 gsm. In various embodiments, the distribution layer 140 can be a meltblown microfiber web of polypropylene material and can have a basis weight from about 10 or 20 gsm to about 30, 50 or 100 gsm. In various embodiments, the meltblown microfiber web can be treated with wetting agents for adequate handling of body exudates. Examples of wetting agents can include, but are not limited to, surface active agents (or surfactants) having a hydrophilic lipophilic balance (HLB) of at least 6, 7 or 18. A variety of surfactants can be used and can include, but are not limited to, anionic, cationic, or neutral from a charge standpoint. Mixtures of surfactants and other wetting agents can also be used. A wetting agent add-on can range from about 0.1 or 0.2% to about 5 or 10%. In various embodiments, an add-on amount can be higher than 10%. For example, the meltblown microfiber web can be treated to impart hydrophlicity by either Aerosol GPG of Cytec or Ahcovel Base N-62 for example. Such material is available from Yuhan-Kimberly Ltd., Seoul, Korea and FlberTex, Malaysia.

Wings:

The wings 26 can be constructed from materials described above with respect to the topsheet layer 20 and the backsheet layer 22. In various embodiments, the wings 26 can comprise an extension of a layer of material within the topsheet layer 20 and/or the backsheet layer 22. By way of example, the wings 26 can be formed by an extension of the topsheet layer 20 and backsheet layer 22 that are then bonded together along peripheral seal 24. Such wings 26 can be integrally formed with the main portion of the absorbent article 10. Alternatively, the wings 26 can be formed independently and separately attached to an intermediate section of the absorbent article 10. Wings 26 that are made independent of the other components of the absorbent article 10 can be bonded to a portion of the topsheet layer 20 and/or backsheet layer 22. Examples of processes for manufacturing absorbent articles 10 and wings 26 include, but are not limited to, those described in U.S. Pat. No. 4,059,114 to Richards, U.S. Pat. No. 4,862,574 to Hassim, et al., U.S. Pat. No. 5,342,647 to Heindel, et al., U.S. Pat. No. 7,070,672 to Alcantara, et al., U.S. Publication No., 2004/0040650 to Venturino, et al., and international publication WO1997/040804 to Emenaker, et al., each of which are hereby incorporated by reference thereto in its entirety.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges: 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article characterized by comprising:
    a. a longitudinal direction, a transverse direction, and a depth direction;
    b. a longitudinal centerline and a transverse centerline;
    c. a first transverse direction end edge and a second transverse direction end edge;
    d. an opposing pair of longitudinal direction side edges extending between and connecting the first transverse direction end edge and the second transverse direction end edge;
    e. an anterior region, a posterior region, and a central region between the anterior region and the posterior region;
    f. a topsheet layer comprising:
        i. a hydrophilic central layer extending in the longitudinal direction of the absorbent article and symmetrically straddling the longitudinal centerline, the central layer having a first longitudinal direction side edge and a second longitudinal direction side edge;

ii. a semi-hydrophilic first side layer having a first inner edge and in an overlapping configuration with the central layer such that the first inner edge of the first side layer is positioned closer in the transverse direction to the longitudinal centerline than the first longitudinal direction side edge of the central layer; and iii. a semi-hydrophilic second side layer having a second inner edge and in an overlapping configuration with the central layer such that the second inner edge of the second side layer is positioned closer in the transverse direction to the longitudinal centerline than the second longitudinal direction side edge of the central layer;

iv. a first region of overlap bordered by the first longitudinal direction side edge of the central layer, the first inner edge of the first side layer, a first portion of the first transverse direction end edge of the absorbent article, and a first portion of the second transverse direction end edge of the absorbent article;

v. a second region of overlap bordered by the second longitudinal direction side edge of the central layer, the second inner edge of the second side layer, a second portion of the first transverse direction end edge of the absorbent article, and a second portion of the second transverse direction end edge of the absorbent article;

vi. a first body facing surface of the first region of overlap has a first area wherein from 10% to 35% of the first area contains a first embossment;

vii. a second body facing surface of the second region of overlap has a second area wherein 10% to 35% of the second area contains a second embossment;

g. a backsheet layer; and h. an absorbent core positioned between the topsheet layer and the backsheet layer and having a first depression located in the depth direction beneath the first embossment and a second depression located in the depth direction beneath the second embossment.

2. The absorbent article of claim 1 wherein the hydrophilic central layer has a water contact angle at or below 59°.

3. The absorbent article of claim 1 wherein each of the semi-hydrophilic first side layer and semi-hydrophilic second side layer have a water contact angle from 60° to 89°.

4. The absorbent article of claim 1 wherein the topsheet layer comprises an exposed region which has a width in the transverse direction between the first inner edge of the first side layer and the second inner edge of the second side layer of from 10 mm to 40 mm.

5. The absorbent article of claim 1 wherein the first region of overlap has a width in the transverse direction between the first longitudinal direction side edge of the central layer and the first inner edge of the first side layer of greater than 10 mm.

6. The absorbent article of claim 1 wherein the second region of overlap has a width in the transverse direction between the second longitudinal direction side edge of the central layer and the second inner edge of the second side layer of greater than 10 mm.

7. The absorbent article of claim 1 wherein the first embossment extends in the longitudinal direction of the absorbent article and has a portion located in each of the anterior region, posterior region, and central region of the first region of overlap and wherein the second embossment extends in the longitudinal direction of the absorbent article and has a portion located in each of the anterior region, posterior region, and central region of the second region of overlap.

8. The absorbent article of claim 7 further comprising a first plurality of discrete embossments located in the central region of the first region of overlap and a second plurality of discrete embossment located in the central region of the second region of overlap.

9. The absorbent article of claim 7 further comprising a first plurality of discrete embossments evenly distributed throughout the anterior region, posterior region, and central region of the first region of overlap and a second plurality of discrete embossments evenly distributed through the anterior region, posterior region, and central region of the second region of overlap.

10. The absorbent article of claim 7 wherein the first embossment crosses over the first inner edge of the first side layer and connects to a first secondary embossment positioned in the anterior region of the exposed region, the first embossment crossed over the first inner edge of the first side layer and connects to a second secondary embossment positioned in the posterior region of the exposed region, wherein the second embossment crosses over the second inner edge of the second side layer and connects to the first secondary embossment in the anterior region, and wherein the second embossment crosses over the second inner edge of the second side layer and connected to the second secondary embossment in the posterior region.

11. The absorbent article of claim 4 further comprising a secondary embossment in the exposed region.

12. The absorbent article of claim 1 further comprising a surge layer.

13. The absorbent article of claim 1 further comprising a fluid intake layer.

14. The absorbent article of claim 1 further comprising a distribution layer.

* * * * *